United States Patent
Euteneuer et al.

(10) Patent No.: US 11,020,111 B2
(45) Date of Patent: Jun. 1, 2021

(54) FASTENERS AND FASTENER DELIVERY DEVICES FOR AFFIXING SHEET-LIKE MATERIALS TO BONE OR TISSUE

(71) Applicant: ROTATION MEDICAL, INC., Plymouth, MN (US)

(72) Inventors: Charles L. Euteneuer, St. Michael, MN (US); Rebecca McCarville, Spring Park, MN (US); Duane Frion, Brooklyn Center, MN (US)

(73) Assignee: ROTATION MEDICAL, INC., Plymouth, MN (US)

( * ) Notice: Subject to any disclaimer, the term of this patent is extended or adjusted under 35 U.S.C. 154(b) by 726 days.

(21) Appl. No.: 15/160,340

(22) Filed: May 20, 2016

(65) Prior Publication Data

US 2016/0262747 A1    Sep. 15, 2016

Related U.S. Application Data

(63) Continuation of application No. 13/889,737, filed on May 8, 2013, now Pat. No. 9,566,063, which is a (Continued)

(51) Int. Cl.
*A61B 17/068* (2006.01)
*A61B 17/064* (2006.01)
(Continued)

(52) U.S. Cl.
CPC ........ *A61B 17/068* (2013.01); *A61B 17/0642* (2013.01); *A61B 17/0682* (2013.01);
(Continued)

(58) Field of Classification Search
CPC ... A61B 17/068; A61B 17/0642; A61B 17/08; A61B 2017/564; A61F 2/0811
(Continued)

(56) References Cited

U.S. PATENT DOCUMENTS

| 511,238 A | 12/1893 | Hieatzman et al. |
| 765,793 A | 7/1904 | Ruckel |

(Continued)

FOREIGN PATENT DOCUMENTS

| CA | 2390508 A1 | 5/2001 |
| EP | 0142225 A1 | 5/1985 |

(Continued)

OTHER PUBLICATIONS

"Rotator Cuff Tear," Wikipedia, the free encyclopedia, 14 pages, Downloaded on Dec. 6, 2012.

(Continued)

*Primary Examiner* — Michelle Lopez
(74) *Attorney, Agent, or Firm* — Seager, Tufte & Wickhem LLP.

(57) ABSTRACT

An improved method for attaching a sheet-like implant to tissue or bone with a fastener having a first and second arm, and a bridge extending therebetween. Each of the first and second arms include a trunk portion including a longitudinally displaced first and second projections extending in opposite directions within a plane defined by the trunk portions. The method includes forming first and second pilot holes in the tissue or bone using a trocar, receiving the first and second trunk portions within their respective pilot holes, and applying a pullout force on the bridge to create an in-plane torque on each trunk such that the resistance to pullout is increased.

15 Claims, 19 Drawing Sheets

Related U.S. Application Data continuation of application No. 13/717,493, filed on Dec. 17, 2012, now Pat. No. 9,370,356.

(60) Provisional application No. 61/577,626, filed on Dec. 19, 2011.

(51) Int. Cl.
    *A61B 17/08* (2006.01)
    *A61F 2/08* (2006.01)
    *A61B 17/56* (2006.01)

(52) U.S. Cl.
    CPC ............ *A61B 17/08* (2013.01); *A61F 2/0811* (2013.01); *A61B 2017/564* (2013.01)

(58) Field of Classification Search
    USPC ........................................ 227/175.1; 128/898
    See application file for complete search history.

(56) References Cited

U.S. PATENT DOCUMENTS

| | | |
|---|---|---|
| 1,728,316 A | 9/1929 | Von Wachenfeldt |
| 1,855,546 A | 4/1932 | File |
| 1,868,100 A | 7/1932 | Goodstein |
| 1,910,688 A | 5/1933 | Goodstein |
| 1,940,351 A | 12/1933 | Howard |
| 2,034,785 A | 3/1936 | Wappler |
| 2,075,508 A | 3/1937 | Davidson |
| 2,131,321 A | 9/1938 | Hart |
| 2,158,242 A | 5/1939 | Maynard |
| 2,199,025 A | 4/1940 | Conn |
| 2,201,610 A | 5/1940 | Dawson, Jr. |
| 2,254,620 A | 9/1941 | Miller |
| 2,277,931 A | 3/1942 | Moe |
| 2,283,814 A | 5/1942 | La Place |
| 2,316,297 A | 4/1943 | Southerland et al. |
| 2,421,193 A | 5/1947 | Gardner |
| 2,571,813 A | 10/1951 | Austin |
| 2,630,316 A | 3/1953 | Foster |
| 2,684,070 A | 7/1954 | Kelsey |
| 2,744,251 A | 5/1956 | Vollmer |
| 2,790,341 A | 4/1957 | Keep et al. |
| 2,817,339 A | 12/1957 | Sullivan |
| 2,825,162 A | 3/1958 | Flood |
| 2,881,762 A | 4/1959 | Lowrie |
| 2,910,067 A | 10/1959 | White |
| 3,068,870 A | 12/1962 | Levin |
| 3,077,812 A | 2/1963 | Dietrich |
| 3,103,666 A | 9/1963 | Bone |
| 3,123,077 A | 3/1964 | Alcamo |
| 3,209,754 A | 10/1965 | Brown |
| 3,221,746 A | 12/1965 | Noble |
| 3,470,834 A | 10/1969 | Bone |
| 3,527,223 A | 9/1970 | Shein |
| 3,570,497 A | 3/1971 | Lemole |
| 3,577,837 A | 5/1971 | Bader, Jr. |
| 3,579,831 A | 5/1971 | Stevens et al. |
| 3,643,851 A | 2/1972 | Green et al. |
| 3,687,138 A | 8/1972 | Jarvik |
| 3,716,058 A | 2/1973 | Tanner, Jr. |
| 3,717,294 A | 2/1973 | Green |
| 3,757,629 A | 9/1973 | Schneider |
| 3,777,538 A | 12/1973 | Weatherly et al. |
| 3,837,555 A | 9/1974 | Green |
| 3,845,772 A | 11/1974 | Smith |
| 3,875,648 A | 4/1975 | Bone |
| 3,960,147 A | 6/1976 | Murray |
| 3,976,079 A | 8/1976 | Samuels et al. |
| 4,014,492 A | 3/1977 | Rothfuss |
| 4,127,227 A | 11/1978 | Green |
| 4,259,959 A | 4/1981 | Walker |
| 4,263,903 A | 4/1981 | Griggs |
| 4,265,226 A | 5/1981 | Cassimally |
| 4,317,451 A | 3/1982 | Cerwin et al. |
| 4,400,833 A | 8/1983 | Kurland |
| 4,422,567 A | 12/1983 | Haynes |
| 4,454,875 A | 6/1984 | Pratt et al. |
| 4,480,641 A | 11/1984 | Failla et al. |
| 4,485,816 A | 12/1984 | Krumme |
| 4,526,174 A | 7/1985 | Froehlich |
| 4,549,545 A | 10/1985 | Levy |
| 4,570,623 A | 2/1986 | Ellison et al. |
| 4,595,007 A | 6/1986 | Mericle |
| 4,610,251 A | 9/1986 | Kumar |
| 4,624,254 A | 11/1986 | McGarry et al. |
| 4,627,437 A | 12/1986 | Bedi et al. |
| 4,632,100 A | 12/1986 | Somers et al. |
| 4,635,637 A | 1/1987 | Schreiber |
| 4,669,473 A | 6/1987 | Richards et al. |
| 4,696,300 A | 9/1987 | Anderson |
| 4,719,917 A | 1/1988 | Barrows et al. |
| 4,738,255 A | 4/1988 | Goble et al. |
| 4,741,330 A | 5/1988 | Hayhurst |
| 4,762,260 A | 8/1988 | Richards et al. |
| 4,799,495 A | 1/1989 | Hawkins et al. |
| 4,809,695 A | 3/1989 | Gwathmey et al. |
| 4,851,005 A | 7/1989 | Hunt et al. |
| 4,858,608 A | 8/1989 | McQuilkin |
| 4,884,572 A | 12/1989 | Bays et al. |
| 4,887,601 A | 12/1989 | Richards |
| 4,924,866 A | 5/1990 | Yoon |
| 4,930,674 A | 6/1990 | Barak |
| 4,968,315 A | 11/1990 | Gattuma |
| 4,976,715 A | 12/1990 | Bays et al. |
| 4,994,073 A | 2/1991 | Green |
| 4,997,436 A | 3/1991 | Oberlander |
| 5,002,563 A | 3/1991 | Pyka et al. |
| 5,013,316 A | 5/1991 | Goble et al. |
| 5,015,249 A | 5/1991 | Nakao et al. |
| 5,037,422 A | 8/1991 | Hayhurst et al. |
| 5,041,129 A | 8/1991 | Hayhurst et al. |
| 5,046,513 A | 9/1991 | Gattuma et al. |
| 5,053,047 A | 10/1991 | Yoon |
| 5,059,206 A | 10/1991 | Winters |
| 5,062,563 A | 11/1991 | Green et al. |
| 5,100,417 A | 3/1992 | Cerier et al. |
| 5,102,421 A | 4/1992 | Anspach, Jr. |
| 5,116,357 A | 5/1992 | Eberbach |
| 5,122,155 A | 6/1992 | Eberbach |
| 5,123,913 A | 6/1992 | Wilk et al. |
| RE34,021 E | 8/1992 | Mueller et al. |
| 5,141,515 A | 8/1992 | Eberbach |
| 5,141,520 A | 8/1992 | Goble et al. |
| 5,156,609 A | 10/1992 | Nakao et al. |
| 5,156,616 A | 10/1992 | Meadows et al. |
| 5,167,665 A | 12/1992 | McKinney |
| 5,171,259 A | 12/1992 | Inoue |
| 5,171,273 A | 12/1992 | Silver et al. |
| 5,174,295 A | 12/1992 | Christian et al. |
| 5,174,487 A | 12/1992 | Rothfuss et al. |
| 5,176,682 A | 1/1993 | Chow |
| 5,176,692 A | 1/1993 | Wilk et al. |
| 5,203,787 A | 4/1993 | Noblitt et al. |
| 5,217,472 A | 6/1993 | Green et al. |
| 5,224,946 A | 7/1993 | Hayhurst et al. |
| 5,242,457 A | 9/1993 | Akopov et al. |
| 5,246,441 A | 9/1993 | Ross et al. |
| 5,251,642 A | 10/1993 | Handlos |
| 5,261,914 A | 11/1993 | Warren |
| 5,269,753 A | 12/1993 | Wilk |
| 5,269,783 A | 12/1993 | Sander |
| 5,282,829 A | 2/1994 | Hermes |
| 5,289,963 A | 3/1994 | McGarry et al. |
| 5,290,217 A | 3/1994 | Campos |
| 5,304,187 A | 4/1994 | Green et al. |
| 5,333,624 A | 8/1994 | Tovey |
| 5,342,396 A | 8/1994 | Cook |
| 5,350,400 A | 9/1994 | Esposito et al. |
| 5,352,229 A | 10/1994 | Goble et al. |
| 5,354,292 A | 10/1994 | Braeuer et al. |
| 5,364,408 A | 11/1994 | Gordon |
| 5,366,460 A | 11/1994 | Eberbach |
| 5,370,650 A | 12/1994 | Tovey et al. |

(56) References Cited

U.S. PATENT DOCUMENTS

| | | |
|---|---|---|
| 5,372,604 A | 12/1994 | Trott |
| 5,374,268 A * | 12/1994 | Sander .................. A61B 17/06 606/148 |
| 5,380,334 A | 1/1995 | Torrie et al. |
| 5,383,477 A | 1/1995 | DeMatteis |
| 5,397,332 A | 3/1995 | Kammerer et al. |
| 5,403,326 A | 4/1995 | Harrison et al. |
| 5,405,360 A | 4/1995 | Tovey |
| 5,411,522 A | 5/1995 | Trott |
| 5,411,523 A | 5/1995 | Goble |
| 5,417,691 A | 5/1995 | Hayhurst |
| 5,417,712 A | 5/1995 | Whittaker et al. |
| 5,425,490 A | 6/1995 | Goble et al. |
| 5,441,502 A | 8/1995 | Bartlett |
| 5,441,508 A | 8/1995 | Gazielly et al. |
| 5,456,720 A | 10/1995 | Schultz et al. |
| 5,464,403 A | 11/1995 | Kieturakis et al. |
| 5,478,354 A | 12/1995 | Tovey et al. |
| 5,486,197 A | 1/1996 | Le et al. |
| 5,497,933 A | 3/1996 | DeFonzo et al. |
| 5,500,000 A | 3/1996 | Feagin et al. |
| 5,501,695 A | 3/1996 | Anspach, Jr. et al. |
| 5,503,623 A | 4/1996 | Tilton, Jr. |
| 5,505,735 A | 4/1996 | Li |
| 5,507,754 A | 4/1996 | Green et al. |
| 5,520,700 A | 5/1996 | Beyar et al. |
| 5,522,817 A | 6/1996 | Sander et al. |
| 5,545,180 A | 8/1996 | Le et al. |
| 5,560,532 A | 10/1996 | DeFonzo et al. |
| 5,562,689 A | 10/1996 | Green et al. |
| 5,569,306 A | 10/1996 | Thal |
| 5,582,616 A | 12/1996 | Bolduc et al. |
| 5,584,835 A | 12/1996 | Greenfield |
| 5,618,314 A | 4/1997 | Harwin et al. |
| 5,622,257 A | 4/1997 | Deschenes et al. |
| 5,628,751 A | 5/1997 | Sander et al. |
| 5,643,319 A | 7/1997 | Green et al. |
| 5,643,321 A | 7/1997 | McDevitt |
| 5,647,874 A | 7/1997 | Hayhurst |
| 5,649,963 A | 7/1997 | McDevitt |
| 5,662,683 A | 9/1997 | Kay |
| 5,667,513 A | 9/1997 | Torrie et al. |
| 5,674,245 A | 10/1997 | Ilgen |
| 5,681,342 A | 10/1997 | Benchetrit |
| 5,702,215 A | 12/1997 | Li |
| 5,713,903 A | 2/1998 | Sander et al. |
| 5,720,753 A | 2/1998 | Sander et al. |
| 5,725,541 A | 3/1998 | Anspach, III et al. |
| 5,741,282 A | 4/1998 | Anspach, III et al. |
| 5,766,246 A | 6/1998 | Mulhauser et al. |
| 5,782,864 A | 7/1998 | Lizardi |
| 5,797,909 A | 8/1998 | Michelson |
| 5,797,931 A | 8/1998 | Bito et al. |
| 5,797,963 A | 8/1998 | McDevitt |
| 5,807,403 A | 9/1998 | Beyar et al. |
| 5,830,221 A | 11/1998 | Stein et al. |
| 5,836,961 A | 11/1998 | Kieturakis et al. |
| 5,868,762 A | 2/1999 | Cragg et al. |
| 5,873,891 A | 2/1999 | Sohn |
| 5,885,258 A | 3/1999 | Sachdeva et al. |
| 5,885,294 A | 3/1999 | Pedlick et al. |
| 5,893,856 A | 4/1999 | Jacob et al. |
| 5,904,696 A | 5/1999 | Rosenman |
| 5,919,184 A | 7/1999 | Tilton, Jr. |
| 5,922,026 A | 7/1999 | Chin |
| 5,928,244 A | 7/1999 | Tovey et al. |
| 5,948,000 A | 9/1999 | Larsen et al. |
| 5,957,939 A | 9/1999 | Heaven et al. |
| 5,957,953 A | 9/1999 | Dipoto et al. |
| 5,968,044 A | 10/1999 | Nicholson et al. |
| 5,980,557 A | 11/1999 | Iserin et al. |
| 5,989,265 A | 11/1999 | Bouquet De La Joliniere et al. |
| 5,997,552 A | 12/1999 | Person et al. |
| 6,063,088 A | 5/2000 | Winslow |
| 6,156,045 A | 12/2000 | Ulbrich et al. |
| 6,179,840 B1 | 1/2001 | Bowman |
| 6,193,731 B1 | 2/2001 | Oppelt et al. |
| 6,193,733 B1 | 2/2001 | Adams |
| 6,245,072 B1 | 6/2001 | Zdeblick et al. |
| 6,302,885 B1 | 10/2001 | Essiger |
| 6,312,442 B1 | 11/2001 | Kieturakis et al. |
| 6,315,789 B1 | 11/2001 | Cragg |
| 6,318,616 B1 | 11/2001 | Pasqualucci et al. |
| 6,322,563 B1 | 11/2001 | Cummings et al. |
| 6,325,805 B1 | 12/2001 | Ogilvie et al. |
| 6,387,113 B1 | 5/2002 | Hawkins et al. |
| 6,391,333 B1 | 5/2002 | Li et al. |
| 6,413,274 B1 | 7/2002 | Pedros |
| 6,425,900 B1 | 7/2002 | Knodel et al. |
| 6,436,110 B2 | 8/2002 | Bowman et al. |
| 6,447,522 B2 | 9/2002 | Gambale et al. |
| 6,447,524 B1 | 9/2002 | Knodel et al. |
| 6,478,803 B1 | 11/2002 | Kapec et al. |
| 6,482,178 B1 | 11/2002 | Andrews et al. |
| 6,482,210 B1 | 11/2002 | Skiba et al. |
| 6,506,190 B1 | 1/2003 | Walshe |
| 6,511,499 B2 | 1/2003 | Schmieding et al. |
| 6,517,564 B1 | 2/2003 | Grafton et al. |
| 6,524,316 B1 | 2/2003 | Nicholson et al. |
| 6,527,795 B1 | 3/2003 | Lizardi |
| 6,530,933 B1 | 3/2003 | Yeung et al. |
| 6,540,769 B1 | 4/2003 | Miller, III |
| 6,551,333 B2 | 4/2003 | Kuhns et al. |
| 6,554,852 B1 * | 4/2003 | Oberlander ........ A61B 17/0401 606/104 |
| 6,569,186 B1 | 5/2003 | Winters et al. |
| 6,575,976 B2 | 6/2003 | Grafton |
| 6,599,286 B2 | 7/2003 | Campin et al. |
| 6,620,185 B1 | 9/2003 | Harvie et al. |
| 6,629,988 B2 | 10/2003 | Weadock |
| 6,638,297 B1 | 10/2003 | Huitema |
| 6,648,893 B2 | 11/2003 | Dudasik |
| 6,666,872 B2 | 12/2003 | Barreiro et al. |
| 6,673,094 B1 | 1/2004 | McDevitt et al. |
| 6,685,728 B2 | 2/2004 | Sinnott et al. |
| 6,692,506 B1 | 2/2004 | Ory et al. |
| 6,723,099 B1 | 4/2004 | Goshert |
| 6,726,704 B1 | 4/2004 | Loshakove et al. |
| 6,726,705 B2 | 4/2004 | Peterson et al. |
| 6,740,100 B2 | 5/2004 | Demopulos et al. |
| 6,746,472 B2 | 6/2004 | Frazier et al. |
| 6,764,500 B1 | 7/2004 | Muijs Van De Moer et al. |
| 6,770,073 B2 | 8/2004 | McDevitt et al. |
| 6,779,701 B2 | 8/2004 | Bailly et al. |
| 6,800,081 B2 | 10/2004 | Parodi |
| 6,835,206 B2 | 12/2004 | Jackson |
| 6,849,078 B2 | 2/2005 | Durgin et al. |
| 6,887,259 B2 | 5/2005 | Lizardi |
| 6,926,723 B1 | 8/2005 | Mulhauser et al. |
| 6,932,834 B2 | 8/2005 | Lizardi et al. |
| 6,939,365 B1 | 9/2005 | Fogarty et al. |
| 6,946,003 B1 | 9/2005 | Wolowacz et al. |
| 6,949,117 B2 | 9/2005 | Gambale et al. |
| 6,964,685 B2 | 11/2005 | Murray et al. |
| 6,966,916 B2 | 11/2005 | Kumar |
| 6,972,027 B2 | 12/2005 | Fallin et al. |
| 6,984,241 B2 | 1/2006 | Lubbers et al. |
| 6,991,597 B2 | 1/2006 | Gellman et al. |
| 7,008,435 B2 | 3/2006 | Cummins |
| 7,021,316 B2 | 4/2006 | Leiboff |
| 7,025,772 B2 | 4/2006 | Gellman et al. |
| 7,033,379 B2 | 4/2006 | Peterson |
| 7,037,324 B2 | 5/2006 | Martinek |
| 7,048,171 B2 | 5/2006 | Thornton et al. |
| 7,063,711 B1 | 6/2006 | Loshakove et al. |
| 7,083,638 B2 | 8/2006 | Foerster |
| 7,087,064 B1 | 8/2006 | Hyde |
| 7,112,214 B2 | 9/2006 | Peterson et al. |
| 7,118,581 B2 | 10/2006 | Fridén |
| 7,144,413 B2 | 12/2006 | Wilford et al. |
| 7,144,414 B2 | 12/2006 | Harvie et al. |
| 7,150,750 B2 | 12/2006 | Damarati |
| 7,153,314 B2 | 12/2006 | Laufer et al. |
| 7,160,314 B2 | 1/2007 | Sgro et al. |

(56) References Cited

U.S. PATENT DOCUMENTS

| | | |
|---|---|---|
| 7,160,326 B2 | 1/2007 | Ball |
| 7,163,551 B2 | 1/2007 | Anthony et al. |
| 7,163,563 B2 | 1/2007 | Schwartz et al. |
| 7,169,157 B2 | 1/2007 | Kayan |
| 7,189,251 B2 | 3/2007 | Kay |
| 7,201,754 B2 | 4/2007 | Stewart et al. |
| 7,214,232 B2 | 5/2007 | Bowman et al. |
| 7,226,469 B2 | 6/2007 | Benavitz et al. |
| 7,229,452 B2 | 6/2007 | Kayan |
| 7,247,164 B1 | 7/2007 | Ritchart et al. |
| 7,303,577 B1 | 12/2007 | Dean |
| 7,309,337 B2 | 12/2007 | Colleran et al. |
| 7,320,692 B1 | 1/2008 | Bender et al. |
| 7,320,701 B2 | 1/2008 | Haut et al. |
| 7,322,935 B2 | 1/2008 | Palmer et al. |
| 7,326,231 B2 | 2/2008 | Phillips et al. |
| 7,343,920 B2 | 3/2008 | Toby et al. |
| 7,368,124 B2 | 5/2008 | Chun et al. |
| 7,377,934 B2 | 5/2008 | Lin et al. |
| 7,381,213 B2 | 6/2008 | Lizardi |
| 7,390,329 B2 | 6/2008 | Westra et al. |
| 7,399,304 B2 | 7/2008 | Gambale et al. |
| 7,404,824 B1 | 7/2008 | Webler et al. |
| 7,416,554 B2 | 8/2008 | Lam et al. |
| 7,452,368 B2 | 11/2008 | Liberatore et al. |
| 7,460,913 B2 | 12/2008 | Kuzma et al. |
| 7,463,933 B2 | 12/2008 | Wahlstrom et al. |
| 7,465,308 B2 | 12/2008 | Sikora et al. |
| 7,481,832 B1 | 1/2009 | Meridew et al. |
| 7,485,124 B2 | 2/2009 | Kuhns et al. |
| 7,497,854 B2 | 3/2009 | Gill et al. |
| 7,500,972 B2 | 3/2009 | Voegele et al. |
| 7,500,980 B2 | 3/2009 | Gill et al. |
| 7,500,983 B1 | 3/2009 | Kaiser et al. |
| 7,503,474 B2 | 3/2009 | Hillstead et al. |
| 7,506,791 B2 | 3/2009 | Omaits et al. |
| 7,559,941 B2 | 7/2009 | Zannis et al. |
| 7,572,276 B2 | 8/2009 | Lim et al. |
| 7,585,311 B2 | 9/2009 | Green et al. |
| 7,766,208 B2 | 8/2010 | Epperly et al. |
| 7,771,440 B2 | 8/2010 | Ortiz et al. |
| 7,776,057 B2 | 8/2010 | Laufer et al. |
| 7,780,685 B2 | 8/2010 | Hunt et al. |
| 7,785,255 B2 | 8/2010 | Malkani |
| 7,807,192 B2 | 10/2010 | Li et al. |
| 7,819,880 B2 | 10/2010 | Zannis et al. |
| 7,918,879 B2 | 4/2011 | Yeung et al. |
| 8,114,101 B2 | 2/2012 | Criscuolo et al. |
| 8,197,837 B2 | 6/2012 | Jamiolkowski et al. |
| 9,107,661 B2 | 8/2015 | Euteneuer et al. |
| 9,198,751 B2 | 12/2015 | Euteneuer et al. |
| 9,247,978 B2 | 2/2016 | Euteneuer et al. |
| 9,271,726 B2 | 3/2016 | Euteneuer |
| 9,314,314 B2 | 4/2016 | Euteneuer et al. |
| 2002/0077687 A1 | 6/2002 | Ahn |
| 2002/0090725 A1 | 7/2002 | Simpson et al. |
| 2002/0123767 A1 | 9/2002 | Prestel |
| 2002/0165559 A1 | 11/2002 | Grant et al. |
| 2003/0073979 A1 | 4/2003 | Naimark et al. |
| 2003/0125748 A1 | 7/2003 | Li et al. |
| 2003/0212456 A1 | 11/2003 | Lipchitz et al. |
| 2004/0059416 A1 | 3/2004 | Murray et al. |
| 2004/0138705 A1* | 7/2004 | Heino .............. A61B 17/064 606/219 |
| 2004/0167519 A1 | 8/2004 | Weiner et al. |
| 2005/0015021 A1 | 1/2005 | Shiber |
| 2005/0049618 A1 | 3/2005 | Masuda et al. |
| 2005/0051597 A1 | 3/2005 | Toledano |
| 2005/0059996 A1 | 3/2005 | Bauman et al. |
| 2005/0060033 A1 | 3/2005 | Vacanti et al. |
| 2005/0107807 A1 | 5/2005 | Nakao |
| 2005/0113736 A1 | 5/2005 | Orr et al. |
| 2005/0171569 A1 | 8/2005 | Girard et al. |
| 2005/0187576 A1 | 8/2005 | Whitman et al. |
| 2005/0240222 A1 | 10/2005 | Shipp |
| 2005/0274768 A1 | 12/2005 | Cummins et al. |
| 2006/0074423 A1 | 4/2006 | Alleyne et al. |
| 2006/0178743 A1 | 8/2006 | Carter |
| 2006/0235442 A1 | 10/2006 | Huitema |
| 2006/0293760 A1 | 12/2006 | DeDeyne |
| 2007/0078477 A1 | 4/2007 | Heneveld, Sr. et al. |
| 2007/0083236 A1 | 4/2007 | Sikora et al. |
| 2007/0112361 A1 | 5/2007 | Schonholz et al. |
| 2007/0179531 A1 | 8/2007 | Thornes |
| 2007/0185506 A1 | 8/2007 | Jackson |
| 2007/0190108 A1 | 8/2007 | Datta et al. |
| 2007/0219558 A1 | 9/2007 | Deutsch |
| 2007/0270804 A1 | 11/2007 | Chudik |
| 2007/0288023 A1 | 12/2007 | Pellegrino et al. |
| 2008/0027470 A1 | 1/2008 | Hart et al. |
| 2008/0051888 A1 | 2/2008 | Ratcliffe et al. |
| 2008/0065153 A1 | 3/2008 | Allard et al. |
| 2008/0090936 A1 | 4/2008 | Fujimura et al. |
| 2008/0125869 A1 | 5/2008 | Paz et al. |
| 2008/0135600 A1 | 6/2008 | Hiranuma et al. |
| 2008/0173691 A1 | 7/2008 | Mas et al. |
| 2008/0188874 A1 | 8/2008 | Henderson |
| 2008/0188936 A1 | 8/2008 | Ball et al. |
| 2008/0195119 A1 | 8/2008 | Ferree |
| 2008/0200949 A1 | 8/2008 | Hiles et al. |
| 2008/0241213 A1 | 10/2008 | Chun et al. |
| 2008/0272173 A1 | 11/2008 | Coleman et al. |
| 2008/0306408 A1 | 12/2008 | Lo |
| 2008/0312688 A1 | 12/2008 | Nawrocki et al. |
| 2009/0001122 A1 | 1/2009 | Prommersberger et al. |
| 2009/0012521 A1 | 1/2009 | Axelson, Jr. et al. |
| 2009/0030434 A1 | 1/2009 | Paz et al. |
| 2009/0069806 A1 | 3/2009 | De La Mora Levy et al. |
| 2009/0076541 A1 | 3/2009 | Chin et al. |
| 2009/0105535 A1 | 4/2009 | Green et al. |
| 2009/0112085 A1 | 4/2009 | Eby |
| 2009/0134198 A1 | 5/2009 | Knodel et al. |
| 2009/0156986 A1 | 6/2009 | Trenhaile |
| 2009/0156997 A1 | 6/2009 | Trenhaile |
| 2009/0182245 A1 | 7/2009 | Zambelli |
| 2009/0210006 A1* | 8/2009 | Cohen .............. A61B 17/06166 606/232 |
| 2009/0242609 A1 | 10/2009 | Kanner |
| 2010/0145367 A1 | 6/2010 | Ratcliffe |
| 2010/0147922 A1 | 6/2010 | Olson |
| 2010/0163598 A1 | 7/2010 | Belzer |
| 2010/0191332 A1 | 7/2010 | Euteneuer et al. |
| 2010/0211097 A1 | 8/2010 | Hadba et al. |
| 2010/0241227 A1 | 9/2010 | Euteneuer et al. |
| 2010/0249801 A1 | 9/2010 | Sengun et al. |
| 2010/0256675 A1 | 10/2010 | Romans |
| 2010/0274278 A1 | 10/2010 | Fleenor et al. |
| 2010/0292715 A1 | 11/2010 | Nering et al. |
| 2010/0292791 A1 | 11/2010 | Lu et al. |
| 2010/0312250 A1 | 12/2010 | Euteneuer et al. |
| 2010/0312275 A1* | 12/2010 | Euteneuer .......... A61B 17/068 606/219 |
| 2010/0327042 A1 | 12/2010 | Amid et al. |
| 2011/0000950 A1 | 1/2011 | Euteneuer et al. |
| 2011/0004221 A1 | 1/2011 | Euteneuer et al. |
| 2011/0011917 A1 | 1/2011 | Loulmet |
| 2011/0034942 A1 | 2/2011 | Levin et al. |
| 2011/0040310 A1 | 2/2011 | Levin et al. |
| 2011/0040311 A1 | 2/2011 | Levin et al. |
| 2011/0066166 A1 | 3/2011 | Levin et al. |
| 2011/0106154 A1 | 5/2011 | DiMatteo et al. |
| 2011/0114700 A1 | 5/2011 | Baxter, III et al. |
| 2011/0224702 A1 | 9/2011 | Van Kampen et al. |
| 2011/0264149 A1 | 10/2011 | Pappalardo et al. |
| 2012/0100200 A1 | 4/2012 | Belcheva et al. |
| 2012/0160893 A1 | 6/2012 | Harris et al. |
| 2012/0193391 A1 | 8/2012 | Michler et al. |
| 2012/0209401 A1 | 8/2012 | Euteneuer et al. |
| 2012/0211543 A1 | 8/2012 | Euteneuer |
| 2012/0248171 A1 | 10/2012 | Bailly et al. |
| 2012/0316608 A1 | 12/2012 | Foley |
| 2013/0153628 A1 | 6/2013 | Euteneuer |
| 2013/0158554 A1 | 6/2013 | Euteneuer et al. |
| 2013/0158587 A1 | 6/2013 | Euteneuer et al. |

(56) References Cited

U.S. PATENT DOCUMENTS

| | | |
|---|---|---|
| 2013/0158661 A1 | 6/2013 | Euteneuer et al. |
| 2013/0172920 A1 | 7/2013 | Euteneuer et al. |
| 2013/0172997 A1 | 7/2013 | Euteneuer et al. |
| 2013/0184716 A1 | 7/2013 | Euteneuer et al. |
| 2013/0240598 A1 | 9/2013 | Euteneuer et al. |
| 2013/0245627 A1 | 9/2013 | Euteneuer et al. |
| 2013/0245682 A1 | 9/2013 | Euteneuer et al. |
| 2013/0245683 A1 | 9/2013 | Euteneuer et al. |
| 2013/0245706 A1 | 9/2013 | Euteneuer et al. |
| 2013/0245707 A1 | 9/2013 | Euteneuer et al. |
| 2013/0245762 A1 | 9/2013 | Van Kampen et al. |
| 2013/0245774 A1 | 9/2013 | Euteneuer et al. |

FOREIGN PATENT DOCUMENTS

| | | |
|---|---|---|
| EP | 0298400 A1 | 1/1989 |
| EP | 0390613 A1 | 10/1990 |
| EP | 0543499 A1 | 5/1993 |
| EP | 0548998 A1 | 6/1993 |
| EP | 0557963 A1 | 9/1993 |
| EP | 0589306 A2 | 3/1994 |
| EP | 0908152 A1 | 4/1999 |
| EP | 589306 B1 | 8/1999 |
| EP | 1491157 A1 | 12/2004 |
| EP | 1559379 A1 | 8/2005 |
| EP | 1491157 B1 | 11/2008 |
| EP | 2030576 A2 | 3/2009 |
| GB | 2154688 A | 9/1985 |
| GB | 2397240 A | 7/2004 |
| JP | 58188442 A | 11/1983 |
| JP | 2005586122 A | 3/2005 |
| JP | 2006515774 A | 6/2006 |
| WO | 8505025 A1 | 11/1985 |
| WO | 0176456 A2 | 10/2001 |
| WO | 0234140 A2 | 5/2002 |
| WO | 2003105670 A2 | 12/2003 |
| WO | 2004000138 A1 | 12/2003 |
| WO | 2004093690 A1 | 11/2004 |
| WO | 2005016389 A2 | 2/2005 |
| WO | 2006086679 A1 | 8/2006 |
| WO | 2007014910 A1 | 2/2007 |
| WO | 2007030676 A2 | 3/2007 |
| WO | 2007078978 A2 | 7/2007 |
| WO | 2007082088 A2 | 7/2007 |
| WO | 2008111073 A2 | 9/2008 |
| WO | 2008111078 A2 | 9/2008 |
| WO | 2008139473 A2 | 11/2008 |
| WO | 2009079211 A1 | 6/2009 |
| WO | 2009143331 A1 | 11/2009 |
| WO | 2011095890 A2 | 8/2011 |
| WO | 2011128903 A2 | 10/2011 |
| WO | 2013119321 A1 | 8/2013 |

OTHER PUBLICATIONS

Alexander et al., "Ligament and tendon repair with an absorbable polymer-coated carbon fiber stent," Bulletin of the Hospital for Joint Diseases Orthopaedic Institute, 46(2):155-173, 1986.

Bahler et al., "Trabecular bypass stents decrease intraocular pressure in cultured himan anterior segments," Am. J. Opthamology, 138(6):988-994, Dec. 2004.

Chamay et al., "Digital contracture deformity after implantation of a silicone prosthesis: Light and electron microscopic study," The Journal of Hand Surgery, 3(3):266-270, May 1978.

D'Ermo et al., "Our results of the operation of ab externo," Opthalmologica, 168: 347-355, 1971.

France et al., "Biomechanical evaluation of rotator cuff fixation methods," The American Journal of Sports Medicine, 17(2), 1989.

Goodship et al., "An assessment of filamentous carbon fibre for the treatment of tendon injury in the horse," Veterinary Record, 106: 217-221, Mar. 8, 1980.

Hunter et al., "Flexor-tendon reconstruction in severely damaged hands," The Journal of Bone and Joint Surgery (American Volume), 53-A(5): 329-358, Jul. 1971.

Johnstone et al., "Microsurgery of Schlemm's canal and the human aqueous outflow system," Am. J. Opthamology, 16(6): 906-917, Dec. 1973.

Kowalsky et al., "Evaluation of suture abrasion against rotator cuff tendon and proximal humerus bone," Arthroscopy: The Journal of Arthroscopic and Related Surgery, 24(3):329-334, Mar. 2008.

Lee et al., "Aqueous-venous and intraocular pressure. Preliminary report of animal studies," Investigative Opthalmology, 5(1): 59-64, Feb. 1966.

Maepea et al., "The pressures in the episcleral veins, Schlemm's canal and the trabecular meshwork in monkeys: Effects of changes in intraocular pressure," Exp. Eye Res., 49:645-663, 1989.

Nicolle et al., "A silastic tendon prosthesis as an adjunct to flexor tendon grafting: An experimental and clinical evaluation," British Journal of Plastic Surgery, 22(3-4):224-236, 1969.

Rubin et al., "The use of acellular biologic tissue patches in foot and ankle surgery," Clinics in Podiatric Medicine and Surgery, 22:533-552, 2005.

Schultz, "Canaloplasty procedure shows promise for open-angle glaucoma in European study," Ocular Surgery News, 34-35, Mar. 1, 2007.

Spiegel et al., "Schlemm's canal implant: a new method to lower intraocular pressure in patients with POAG," Opthalmic Surgery and Lasers, 30(6):492-494, Jun. 1999.

Stenson et al., "Arthroscopic treatment of partial rotator cuff tears," Operative Techniques in Sports Medicine, 12 (2):135-148, Apr. 2004.

Valdez et al., "Repair of digital flexor tendon lacerations in the horse, using carbon fiber implants," JAYMA, 177(5):427-435, Sep. 1, 1980.

\* cited by examiner

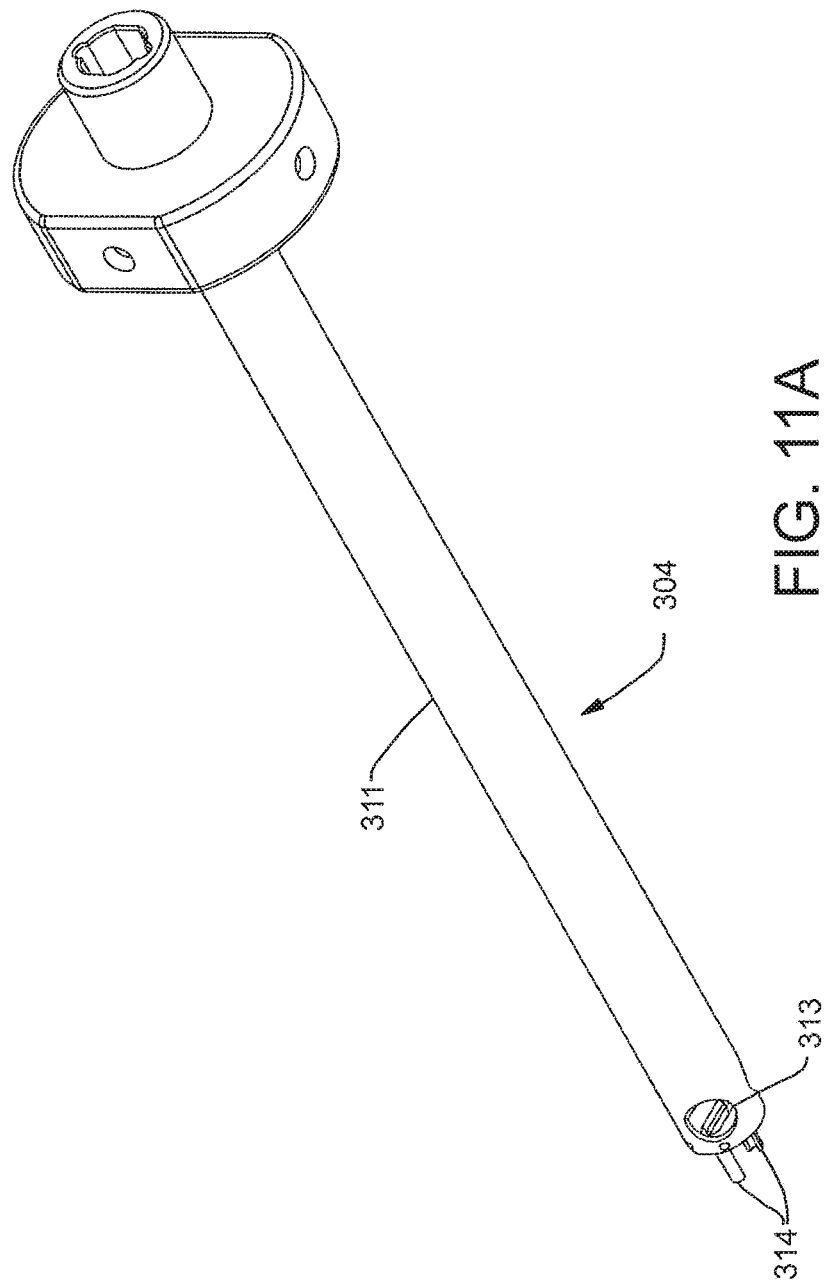

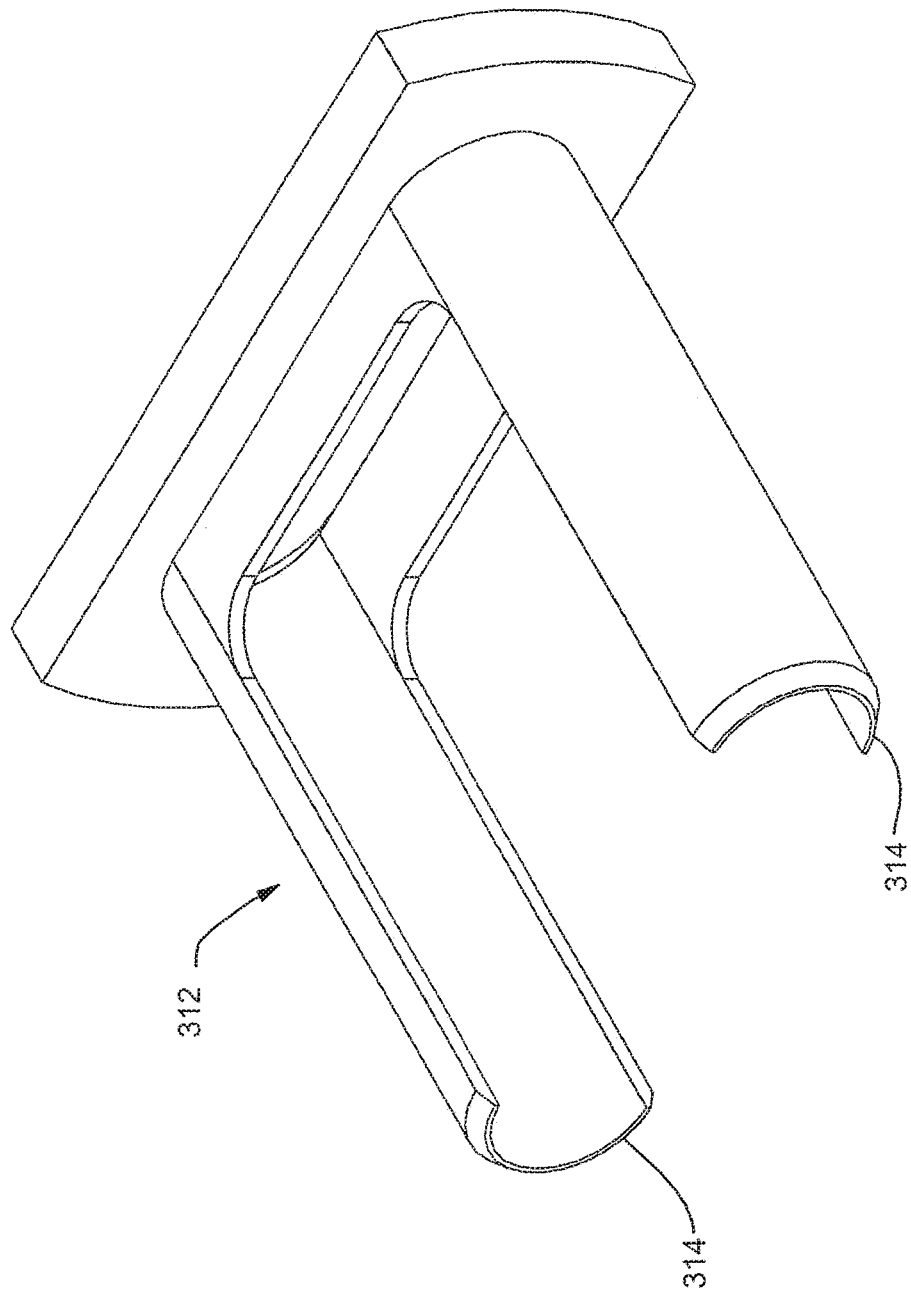

FASTENERS AND FASTENER DELIVERY DEVICES FOR AFFIXING SHEET-LIKE MATERIALS TO BONE OR TISSUE

CROSS REFERENCE TO RELATED APPLICATIONS

This application is a Continuation of U.S. application Ser. No. 13/889,737, filed on May 8, 2013, which is a Continuation of U.S. application Ser. No. 13/717,493 filed on Dec. 17, 2012, which claims the benefit of U.S. Provisional Patent Application Ser. No. 61/577,626 filed on Dec. 19, 2011, the disclosures of each incorporated herein by reference.

The present disclosure is related to the following commonly assigned applications, the disclosures of which are incorporated herein by reference: U.S. Provisional Application No. 61/577,6121 filed on Dec. 19, 2011; U.S. Provisional Application No. 61/577,632 filed on Dec. 19, 2011; and U.S. Provisional Application No. 61/577,635 filed on Dec. 19, 2011.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates generally to orthopedic medicine and surgery. More particularly, the present invention relates to methods and apparatus for delivery and fixation of sheet-like materials, such as for treating tendons or like tissue of articulating joints such as tendons in the rotator cuff of the shoulder.

BACKGROUND

The glenohumeral joint of the shoulder is found where the head of the humerus mates with a shallow depression in the scapula. This shallow depression is known as the glenoid fossa. Six muscles extend between the humerus and scapula and actuate the glenohumeral joint. These six muscles include the deltoid, the teres major, and the four rotator cuff muscles. The rotator cuff muscles are a complex of muscles. The muscles of the rotator cuff include the supraspinatus, the infraspinatus, the subscapularis, and the teres minor. The centering and stabilizing roles played by the rotator cuff muscles are critical to the proper function of the shoulder. The rotator cuff muscles provide a wide variety of moments to rotate the humerus and to oppose unwanted components of the deltoid and pectoral muscle forces.

The muscles of the rotator cuff arise from the scapula. The distal tendons of the rotator cuff muscles splay out and interdigitate to form a common continuous insertion on the humerus. The supraspinatus muscle arises from the supraspinatus fossa of the posterior scapula, passes beneath the acromion and the acromioclavicular joint, and attaches to the superior aspect of the greater tuberosity. The mechanics of the rotator cuff muscles are complex. The rotator cuff muscles rotate the humerus with respect to the scapula, compress the humeral head into the glenoid fossa providing a critical stabilizing mechanism to the shoulder (known as concavity compression), and provide muscular balance. The supraspinatus and deltoid muscles are equally responsible for producing torque about the shoulder joint in the functional planes of motion.

The rotator cuff muscles are critical elements of this shoulder muscle balance equation. The human shoulder has no fixed axis. In a specified position, activation of a muscle creates a unique set of rotational moments. For example, the anterior deltoid can exert moments in forward elevation, internal rotation, and cross-body movement. If forward elevation is to occur without rotation, the cross-body and internal rotation moments of this muscle must be neutralized by other muscles, such as the posterior deltoid and infraspinatus. The timing and magnitude of these balancing muscle effects must be precisely coordinated to avoid unwanted directions of humeral motion. Thus the simplified view of muscles as isolated motors, or as members of force couples must give way to an understanding that all shoulder muscles function together in a precisely coordinated way—opposing muscles canceling out undesired elements leaving only the net torque necessary to produce the desired action. Injury to any of these soft tissues can greatly inhibit ranges and types of motion of the arm.

With its complexity, range of motion and extensive use, a common soft tissue injury is damage to the rotator cuff or rotator cuff tendons. Damage to the rotator cuff is a potentially serious medical condition that may occur during hyperextension, from an acute traumatic tear or from overuse of the joint. With its critical role in abduction, rotational strength and torque production, the most common injury associated with the rotator cuff region is a strain or tear involving the supraspinatus tendon. A tear at the insertion site of the tendon with the humerus, may result in the detachment of the tendon from the bone. This detachment may be partial or full, depending upon the severity of the injury or damage. Additionally, the strain or tear can occur within the tendon itself. Injuries to the supraspinatus tendon and current modalities for treatment are defined by the type and degree of tear. The first type of tear is a full thickness tear, which as the term indicates is a tear that extends through the thickness of the supraspinatus tendon regardless of whether it is completely torn laterally. The second type of tear is a partial thickness tear which is further classified based on how much of the thickness is torn, whether it is greater or less than about 50% of the thickness.

The accepted treatment for a full thickness tear or a partial thickness tear greater than 50% includes reconnecting the torn tendon via sutures. For the partial thickness tears greater than 50%, the tear is completed to a full thickness tear by cutting the tendon prior to reconnection. In contrast to the treatment of a full thickness tear or a partial thickness tear of greater than 50%, the current standard treatment for a partial thickness tear less than 50% usually involves physical cessation from use of the tendon, i.e., rest. Specific exercises can also be prescribed to strengthen and loosen the shoulder area. In many instances, the shoulder does not heal and the partial thickness tear can be the source of chronic pain and stiffness. Further, the pain and stiffness may cause—restricted use of the limb which tends to result in further degeneration or atrophy in the shoulder. Surgical intervention may be required for a partial thickness tear of less than 50%, however, current treatment interventions do not include repair of the tendon, and rather the surgical procedure is directed to arthroscopic removal of bone to relieve points of impingement or create a larger tunnel between the tendon and bone that is believed to be causing tendon damage. As part of the treatment, degenerated tendon may also be removed using a debridement procedure in which tendon material is ablated. Again, the tendon partial thickness tear is not repaired. Several authors have reported satisfactory early post operative results from these procedures, but over time recurrent symptoms have been noted. In the event of recurrent symptoms, many times a patient will "live with the pain". This may result in less use of the arm and shoulder which causes further degeneration of the tendon and may lead to more extensive damage. A tendon repair would then need to be done in a later procedure if the prescribed treatment for the partial tear was unsuccessful in relieving pain and stiffness or over time the tear propagated through injury or degeneration to a full thickness tear or a partial thickness tear greater than 50% with attendant pain and debilitation. A subsequent later procedure would include the more drastic procedure of completing the tear to full thickness and suturing the ends of the tendon back together. This procedure requires extensive rehabilitation, has relatively high failure rates and subjects the patient who first presented and was treated with a partial thickness tear less than 50% to a second surgical procedure.

As described above, adequate treatments do not currently exist for repairing a partial thickness tear of less than 50% in the supraspinatus tendon. Current procedures attempt to alleviate impingement or make room for movement of the tendon to prevent further damage and relieve discomfort but do not repair or strengthen the tendon. Use of the still damaged tendon can lead to further damage or injury. Prior damage may result in degeneration that requires a second more drastic procedure to repair the tendon. Further, if the prior procedure was only partially successful in relieving pain and discomfort, a response may be to use the shoulder less which leads to degeneration and increased likelihood of further injury along with the need for more drastic surgery. Further, it would be beneficial to be able to treat partial thickness tears greater than 50% without cutting the untorn portion of the tendon to complete the tear before suturing back together. There is a large need for surgical techniques and systems to treat partial thickness tears and prevent future tendon damage by strengthening or repairing the native tendon having the partial thickness tear.

SUMMARY OF THE DISCLOSURE

The present disclosure is generally directed to a fastener or staple that can be used to attach an implant to bone or other tissue. The staple or fastener can be included in a kit or system that also can include a staple delivery device and a pilot hole forming trocar assembly. The trocar assembly is used to create pilot holes and retain instrument position within those pilot holes for staple insertion. The staple delivery device can carry the staple into the pilot holes and release the staple in engagement with bone to retain the implant in position.

The staple for insertion and retention in bone can include a bridge portion having arms extending from proximate each end thereof, at least a portion of each arm including tissue retention members, each tissue retention member having at least two barbed projections extending laterally therefrom. Each arm can have a cross sectional area of reduced strength proximate each projection relative to other portions of the tissue retention member such that a portion of the tissue retention member flexes laterally proximate each projection in response to a pullout force applied to the bridge. The tissue retention members can include a trunk of greater cross sectional area than a non-trunk portion of the arms.

The fastener or staple can also include, in alternative embodiments, a first arm having a proximal end and a distal end, a second arm having a proximal end and a distal end, and a bridge connecting the first arm and second arm, wherein each of the first and second arms include a trunk portion extending over at least a portion of the length thereof. Each trunk can have a lateral extent larger than a lateral extent of the bridge or non-trunk arm portion adjacent thereto such that the staple includes a first change in lateral stiffness disposed proximate the bridge or non-trunk arm portion abutment with the first trunk and a second change in lateral stiffness disposed proximate the bridge or non-trunk arm portion abutment with the second trunk. The lateral extent of each trunk in at least one direction can be at least about three times the lateral extent of at least a portion of the bridge or non-trunk portion of the arm.

Each trunk can further include a first projection and a second projection, the first projection including a first proximal surface extending away from the trunk in a first direction, the first direction being such that the first proximal surface will engage the tissue or bone when the trunk is inserted therein so that a first moment is applied to the trunk in response to a pullout force on the bridge. Likewise, the second projection can include a second proximal surface extending away from the trunk in a second direction, the second direction being such that the second proximal surface will engage the tissue or bone when the trunk is inserted therein so that a second moment is applied to the trunk in response to a pullout force on the bridge. Each of the trunks can further include a localized area of weakness proximate the second projection thereon. For example, a second area of reduced strength can include a slit in the cross section of the tissue retention member or trunk adjacent at least one of the projections therefrom. Further, reduced strength can be created where the trunk meets the non-trunk portion of the arm adjacent thereto or the bridge.

In some embodiments, the change in lateral stiffness and the localized area of weakness allow flexing of each arm portion in response to the first and second moment, respectively.

The projections can be arranged to extend in first and second directions to achieve increased pullout strength. The first direction can extend proximally and laterally away from each trunk while the second direction can extend proximally and laterally away from each trunk and a lateral component of the second direction is generally opposite a lateral component of the first direction. The forces on the projections create moments about the more flexible portions of the staple where the direction of the first moment is generally opposite the direction of the second moment on each arm.

In some embodiments, the fastener first trunk and the second trunk each define a cavity, each cavity being spaced laterally from the respective non-trunk portion or bridge adjacent thereto. Each cavity defined by the first and the second trunk is sized to receive a first stake and a second stake, respectively, of a fastener delivery device. Each cavity defined by the first and the second trunk can extend from the proximal end to the distal end of the trunk.

BRIEF DESCRIPTION OF THE DRAWINGS

FIG. 11A is a perspective view of the sheath assembly of FIG. 10B with the trocar removed;

FIG. 11C is a perspective view of one pilot hole position retention member which is positioned in a distal portion of the sheath assembly in one embodiment of the present disclosure;

DETAILED DESCRIPTION

The following detailed description should be read with reference to the drawings in which similar elements in different drawings are numbered the same. The drawings, which are not necessarily to scale, depict illustrative embodiments and are not intended to limit the scope of the invention.

Figure 1:
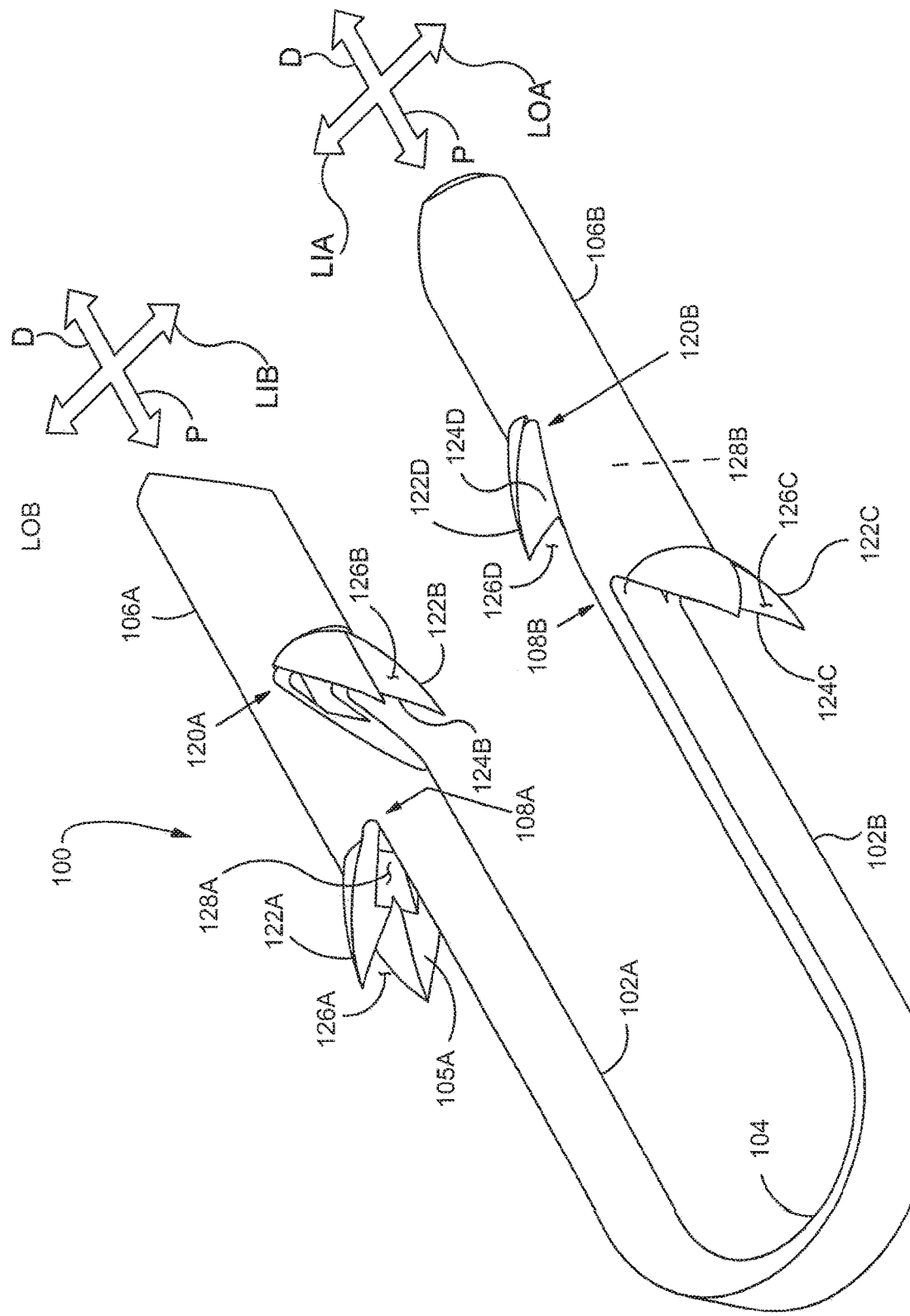
FIG. 1 is a perspective view illustrating an exemplary tissue fastener or staple in accordance with the present disclosure.

FIG. 1 is a perspective view illustrating an exemplary staple 100 in accordance with the present detailed description. With reference to FIG. 1, it will be appreciated that staple 100 may assume various orientations without deviating from the spirit and scope of this detailed description. Although the various parts of this exemplary embodiment are depicted in relative proportion to other parts of the staple 100, other configurations in size and orientation of the various parts are possible. A number of reference directions are illustrated using arrows in FIG. 1 to assist in understanding the details of the staple 100. The illustrated directions include: a proximal direction P, a distal direction D, a first laterally outward direction LOA, a second laterally outward direction LOB, a first laterally inward direction LIA, and a second laterally inward direction LIB.

Staple 100 comprises a first arm 102A, a second arm 102B, and a bridge 104 extending from, abutting or adjacent to the proximal end of first arm 102A to the proximal end of second arm 102B. The first arm 102A includes a first trunk 106A extending for at a least a portion of the length of the first arm 102A. As depicted in FIG. 1, a proximal portion of the first arm 102A abuts the proximal end of the first trunk 106A. The first arm 102A, in this embodiment includes the trunk portion 106A and a non-trunk portion 105A. The length of first trunk 106A relative to the overall length of the first arm 102A can vary in different embodiments. The first trunk 106A can extend for the entire length of the first arm 102A such that the bridge abuts with or is adjacent to the trunk 106A. Similarly, the second arm 102B includes a second trunk 106B extending for at least a portion of the length of the second arm 102B. A proximal portion of the second arm 102B abuts the proximal end of the second trunk 106B. The second arm 102B, in this embodiment includes the trunk portion 106B and a non-trunk portion 105B. The length of second trunk 106B relative to the overall length of the second arm 102B can vary in different embodiments. The second trunk 106B can extend for the entire length of the second arm 102B such that the bridge abuts with or is adjacent to the trunk 106B. In FIG. 1, first trunk 106A and second trunk 106B are shown extending distally from a proximal portion of first arm 102A and second arm 102B, respectively.

In the embodiment of FIG. 1, first trunk 106A has a lateral extent, or cross sectional area, that is larger than a lateral extent of the non-trunk portion 105A of first arm 102A and bridge 104. The staple 100 includes a first change in lateral stiffness 108A disposed where the distal end of non-trunk portion 105A of first arm 102A abuts first trunk 106A. As depicted, the change in stiffness is abrupt, but can be gradual in alternative embodiments. In an embodiment where the first trunk 106A extends for the full length of the first arm 102A, the change in stiffness occurs where the first trunk 106A abuts the bridge 104. With reference to FIG. 1, it will be appreciated that first trunk 106A is mounted eccentrically to first arm 102A and second trunk 106B is mounted eccentrically to second arm 102B. As with first trunk 106A, second trunk 106B has a lateral extent, or cross sectional area that is larger than a lateral extent of second arm 102B or bridge 104. The staple 100 includes a second change in lateral stiffness 108B where the distal end of second arm 102B abuts second trunk 106A in the embodiment of FIG. 1. If the second trunk 106B extends for the entire length of second arm 102B, the change in stiffness occurs at the abutment with the bridge 104.

Each of the first trunk 106A and second trunk 106B can include at least a first projection 122A, 122C and a second projection 122B, 122D, the first projection 122A, 122C on each trunk 106A, 106B includes a first proximal surface 124A, 124C extending away from the trunk in a first direction, the first direction being such that the first proximal surface 124A, 124C will engage the tissue or bone after the trunk is inserted therein and a pullout force is applied to the bridge 104. This force creates a first moment centered on the area of reduced lateral extent adjacent the trunk, tending to rotate the trunk thereabout, further providing a greater holding force in response to the pullout force as the trunk presses against the tissue or bone. The second projection 122B, 122D includes a second proximal surface 124B, 124D extending away from the trunk in a second direction, different from the first direction, the second direction being such that the second proximal surfaces 124B, 124D will engage the tissue or bone after the trunk is inserted therein and a pullout force is applied to the bridge 104. A slit or area of reduced cross section in the trunk adjacent the second projections provide an area of weakness so that a second moment is applied to the trunk in response to a pullout force on the bridge 104. This moment causes rotation of the trunk about the area of weakness and increases the holding force with increased pullout force.

As specifically illustrated in the embodiment of staple or fastener 100 in FIG. 1, first trunk 106A includes a first projection 122A disposed at an outer side of trunk 106A and a second projection 122B disposed at an inner side of the trunk. First projection 122A includes a first proximal surface 124A extending away from first trunk 106A in a first direction. With reference to FIG. 1, it will be appreciated that the first direction has an outward lateral component and a proximal component so that first proximal surface 124A extends outwardly and proximally away from first trunk 106A. The first direction is selected such that first proximal surface 124A will engage tissue or bone proximate the outer side of first trunk 106A after being inserted therein so that a first moment is applied to the trunk in response to a pullout force on bridge 104. The moment centers on the arm portion of lesser cross section adjacent the first projection.

In the embodiment of FIG. 1, first trunk 106A includes a first localized area of weakness 120A disposed proximate second projection 122B. Second projection 122B includes a second proximal surface 124B extending away from first trunk 106A in a second direction. The second direction is selected such that second proximal surface 124A will engage tissue or bone proximate the inner side of first trunk 106A when inserted therein so that a second moment is applied to the trunk in response to a pullout force on bridge 104. The moment centers around the area of weakness 120A. The second moment has a direction that is generally opposite a direction of the first moment. It will be appreciated that the second direction has an inward lateral component and a proximal component so that second proximal surface 124B extends inwardly and proximally away from first trunk 106A.

Second trunk 106B includes a third projection 122C disposed at an outer side of second trunk 106B and a fourth projection 122D disposed at an inner side of the trunk. In the embodiment of FIG. 1, third projection 122C includes a third proximal surface 124C extending away from second trunk 106B in a third direction. With reference to FIG. 1, it will be appreciated that the third direction has an outward lateral component and a proximal component so that third proximal surface 124C extends outwardly and proximally away from second trunk 106B. The third direction is selected such that third proximal surface 124C will engage tissue or bone proximate the outer side of second trunk 106B when inserted therein so that a third moment is applied to the trunk in response to a pullout force on bridge 104.

In the embodiment of FIG. 1, second trunk 106B includes a second localized area of weakness 120B disposed proximate fourth projection 122D. Fourth projection 122D includes a fourth proximal surface 124D extending away from second trunk 106B in a fourth direction. In the embodiment of FIG. 1, the fourth direction is selected such that second proximal surface 124A will engage tissue or bone proximate the inner side of second trunk 106B when inserted therein so that a fourth moment is applied to the trunk in response to a pullout force on bridge 104. The fourth moment has a direction that is generally opposite a direction of the third moment. It will be appreciated that the fourth direction has an inward lateral component and a proximal component so that fourth proximal surface 124D extends inwardly and proximally away from second trunk 106.

As depicted in FIG. 1, the staple 100 includes proximal projections that extend away from or outward from the bridge 104, while the distal projections extend inward or toward the center of the bridge 104. This creates generally opposing forces in response to tension on the bridge which, in combination with areas of weakness or reduced lateral extent, substantially increases the holding force of the staple in bone as the different portions of the trunks tend to rotate in opposite directions and apply force to an opposing wall in the hole in bone in which the staple is positioned. It is however, understood that other configurations of the projections are possible. In some embodiments, at least two projections are included and they extend in different directions to cause different force responses as tension is applied to the bridge. It is believed this provides adequate holding force in bone, which can include differing thicknesses of hard and soft tissue along with porous areas.

In some useful embodiments, each projection of staple 100 may be clefted to form a plurality of points for greater retention in tissue. In the exemplary embodiment of FIG. 1, first projection 122A of first trunk 106A defines a first notch 126A that divides first projection 122A into a first sub-projection and a second sub-projection. Second projection 122B of second trunk 106B defines a second notch 126B. In the exemplary embodiment of FIG. 1, second notch 126B divides second projection 122B into a first sub-projection and a second sub-projection. Third projection 122C of second trunk 106B defines a third notch 126C that divides third projection 122C into a first sub-projection and a second sub-projection. Fourth projection 122D of second trunk 106B defines a fourth notch 126D that divides fourth projection 122D into a first sub-projection and a second sub-projection.

Figures 2, 3:
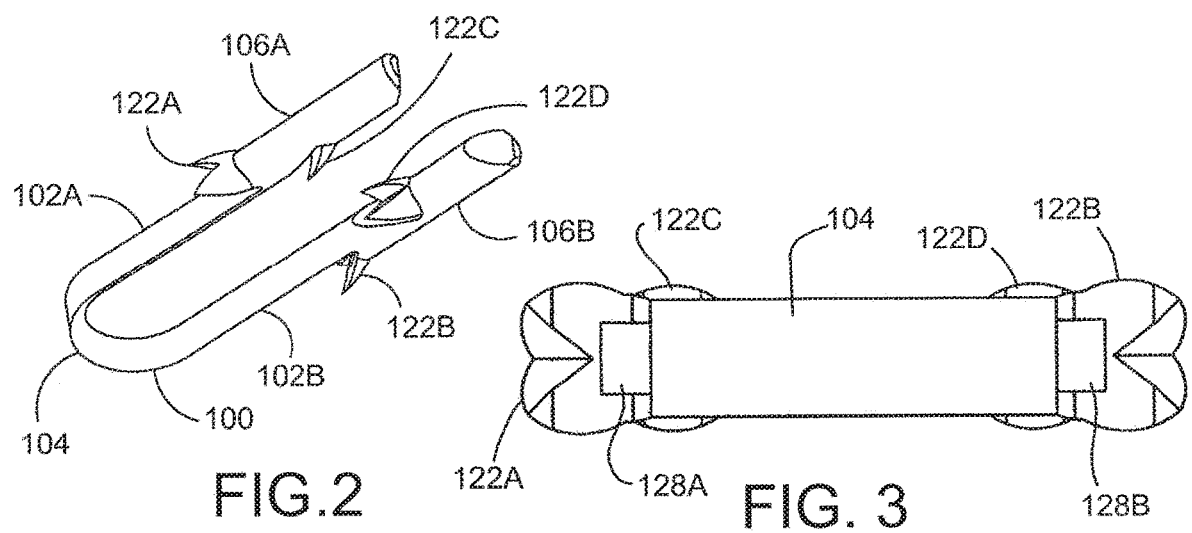
FIG. 2 is a an alternative perspective view of the tissue fastener or staple of FIG. 1 illustrating other features in accordance with the present disclosure.
FIG. 3 is a top plan view of the tissue fastener or staple of FIG. 1 illustrating the laterally extending legs having lumens for receiving the stakes of a delivery device for positioning the staple in desired tissue.

With continued reference to FIG. 1 and further reference to FIGS. 2 and 3, first trunk 106A defines a first cavity 128A and second trunk 106B defines a second cavity 128B. In the exemplary embodiment of FIGS. 1, 2 and 3, first cavity 128A extends into first trunk 106A and second cavity 128B extends into second trunk 106B. The cavity is sized to cooperate with a staple delivery device for holding and inserting the staple into tissue or bone, as later described in detail herein. In summary, the staple delivery device includes longitudinally extending stakes that fit within the cavities 128A, 128B to hold the staple 100 and push it into position in the tissue as the stake abuts a portion of its respective trunk. In some embodiments the cavity may extend through a portion of the length of each trunk, as best depicted in FIG. 2 which indicates the distal end of the staple 100 is closed. Alternatively, first cavity 128A and second cavity 128B may extend through the entire length of each trunk 106A, 106B or other portions of staple 100 in some embodiments. As illustrated by the top view of the staple 100 in FIG. 3, first cavity 128A and second cavity 128B each have a generally rectangular or square cross-sectional shape to cooperate with a similarly shaped cross section on a staple delivery device. However, that first cavity 128A and second cavity 128B may have various cross-sectional shapes to cooperate with alternative staple delivery device designs without deviating from the spirit and scope of the present detailed description.

Figure 4:
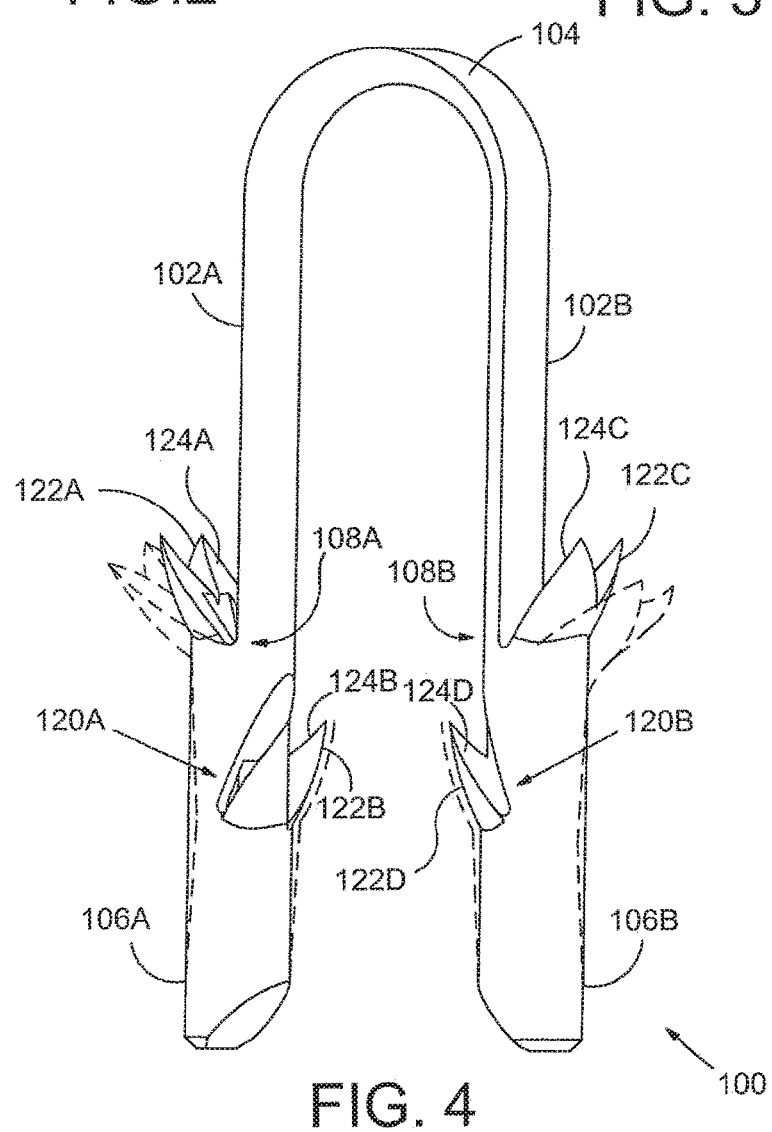
FIG. 4 is a front plan view of the tissue fastener or staple of FIG. 1 illustrating in phantom flexing of the barbs and legs of the staple in response to grasping of tissue in one embodiment of the disclosure.

FIG. 4 is an alternative perspective view of the embodiment in FIG. 1 illustrating an exemplary staple 100 in accordance with the present detailed description. In particular, FIG. 4 illustrates in phantom the flexing and bending of the trunks 106A and 106B after implant in response to tension applied to the bridge, as by tissue or an implant affixed at an implant site. Staple 100 comprises a first arm 102A, a second arm 102B, and a bridge 104 extending from the proximal end of first arm 102A to the proximal end of second arm 102B. The distal end of first arm non-trunk portion 105A abuts the proximal end of first trunk 106A. Similarly, the distal end of second aim non-trunk portion 105B abuts the proximal end of a second trunk 106B. In FIG. 4, first trunk 106A and second trunk 106B are shown extending distally from first arm 102A and second arm 102B, respectively.

In the embodiment of FIG. 4, first trunk 106A has a lateral extent that is larger than the lateral extent of the non-trunk portion 105A of first arm 102A. This combination creates a relatively abrupt change in lateral stiffness 108A disposed where the distal end of the non-trunk portion 108A of first arm 102A abuts first trunk 106A. With reference to FIG. 4, first trunk 106A is mounted eccentrically to first arm 102A and second trunk 106B is mounted eccentrically to second arm 102B, however, other mountings or abutments can be used, such as a non-trunk portion having walls that surround the cavity and include a lumen therethrough to access the cavity with a staple delivery stake. A change in lateral stiffness would still be accomplished where the lateral extend changed. Further, a change in lateral stiffness could be accomplished by using a different material for the non-trunk portion relative to the trunk portion. Second trunk 106B in combination with the non-trunk portion 105B of second arm 102B provides the same change in lateral stiffness 108B. The first arm 102A, the second arm 102B, and the bridge 104 may be integrally formed of a polymeric material, such as polyether ether ketone (PEEK).

As earlier described the configuration of the four projections 122A, 122B, 122C and 122D, contact the tissue or bone and provide a holding force upon implantation. Each projection is positioned to provide a force moment in a desired direction to the trunk in response to the pullout force on the bridge 104.

In the embodiment of FIG. 4, first trunk 106A and second trunk 106B include first and second localized areas of weakness 120A, 120B disposed proximate second projections 122B, 122D. This area of weakness is formed by a slit formed proximal of the projection. However, the area of weakness could be formed by other means, such as a change in material, pinching or perforations.

The combination of projections, areas of weakness and changes in lateral extent provide desired flexing, bending and rotating of the trunk in response to pull out forces once implanted in a bone, such as in a pilot hole formed in the bone. Together these components act as tissue retention members. An exemplary deflected shape is shown with dashed lines in FIG. 4. Staple 100 may be urged to assume the deflected shape shown in FIG. 4, for example, by applying a pullout force on the bridge 104 of the staple 100. Alternatively, distally directed forces can be applied on staple 100 using, for example, the staple delivery system shown later and described herein. In some applications, the staple delivery tool may be used to urge first projection 122A and third projection 122C into orientations which lock staple 100 into a target tissue. For example, first projection 122A and third projection 122C may be rotated so that these projections engage the target tissue. When this is the case, tension extending through bridge 104 of staple 100 may keep first projection 122A and third projection 122C in the rotated position. Also when this is the case, the projections may inhibit staple pullout. Further, rotation of any projection causes a rotational force and within limits defined by the hole in the bone some rotation to an adjacent portion of the trunk which contacts or engages the wall of the hole in the bone. Increased pullout force results in increasing holding force with this design.

Figure 5:
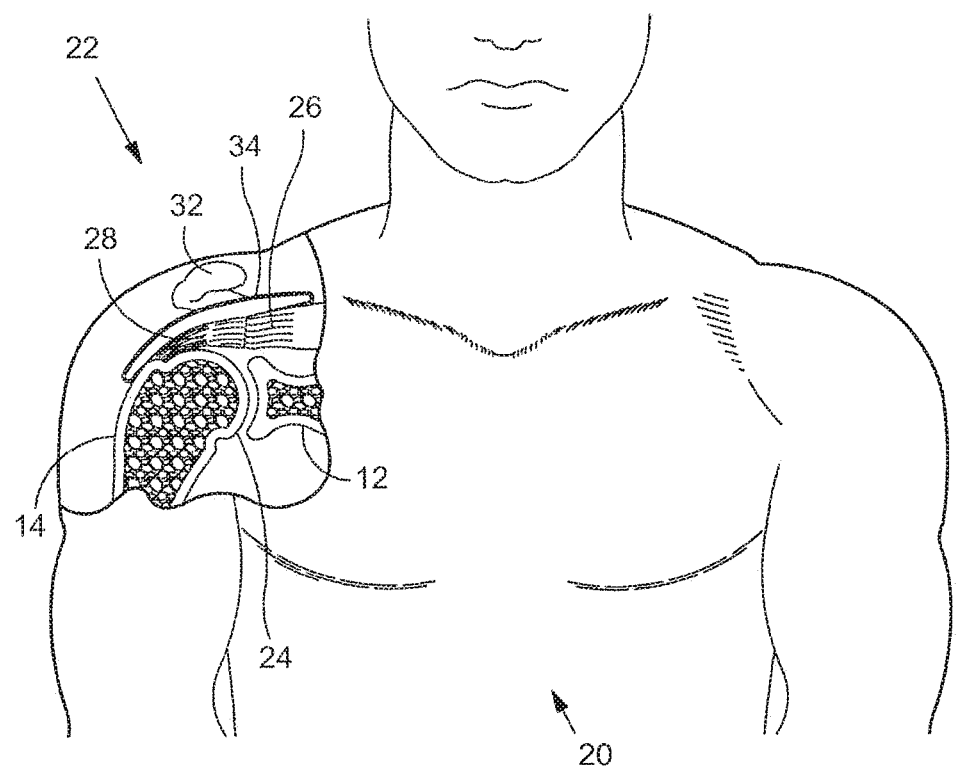
FIG. 5 is a stylized anterior view of a shoulder including a humerus and a scapula.

Next referring to FIG. 5, an exemplary use or application of the staples of the present disclosure is described. FIG. 5 is a stylized anterior view of a patient 20. For purposes of illustration, a shoulder 22 of patient 20 is shown in cross-section in FIG. 5. Shoulder 22 includes a humerus 14 and a scapula 12. In FIG. 5, a head 24 of humerus 14 can be seen mating with a glenoid fossa of scapula 12 at a glenohumeral joint. With reference to FIG. 5, it will be appreciated that the glenoid fossa comprises a shallow depression in scapula 12. The movement of humerus 14 relative to scapula 12 is controlled by a number of muscles including: the deltoid, the supraspinatus, the infraspinatus, the subscapularis, and the teres minor. For purposes of illustration, only the supraspinatus 26 is shown in FIG. 5.

With reference to FIG. 5, a distal tendon 28 of the supraspinatus 26 meets humerus 14 at an insertion point. Scapula 12 of shoulder 22 includes an acromium 32. In FIG. 5, a subcromial bursa 34 is shown extending between acromium 32 of scapula 12 and head 24 of humerus 14. Subcromial bursa 34 is shown overlaying supraspinatus 26 as well as supraspinatus tendon 28 and a portion of humerus 14. Subcromial bursa 34 is one of the hundreds of bursae found the human body. Each bursa comprises a fluid filled sac. The presence of these bursae in the body reduces friction between bodily tissues.

The exemplary staples or fasteners described herein may be used to affix tendon repair implants to various target tissues. The shoulder depicted in FIG. 5 is one example where a tendon repair implant may be affixed to one or more bones associated with an articulating joint, such as the glenohumeral joint. Additionally, the tendon repair implant may be affixed to one or more tendons to be treated. The tendons to be treated may be torn, partially torn, have internal micro-tears, be untorn, and/or be thinned due to age, injury or overuse. Applicants believe that the methods and apparatus of the present application and related devices may provide very beneficial therapeutic effect on a patient experiencing joint pain believed to be caused by partial thickness tears and/or internal microtears. By applying a tendon-repair implant early before a full tear or other injury develops, the implant may cause the tendon to thicken and/or at least partially repair itself, thereby avoiding more extensive joint damage, pain, and the need for more extensive joint repair surgery.

Figure 6:
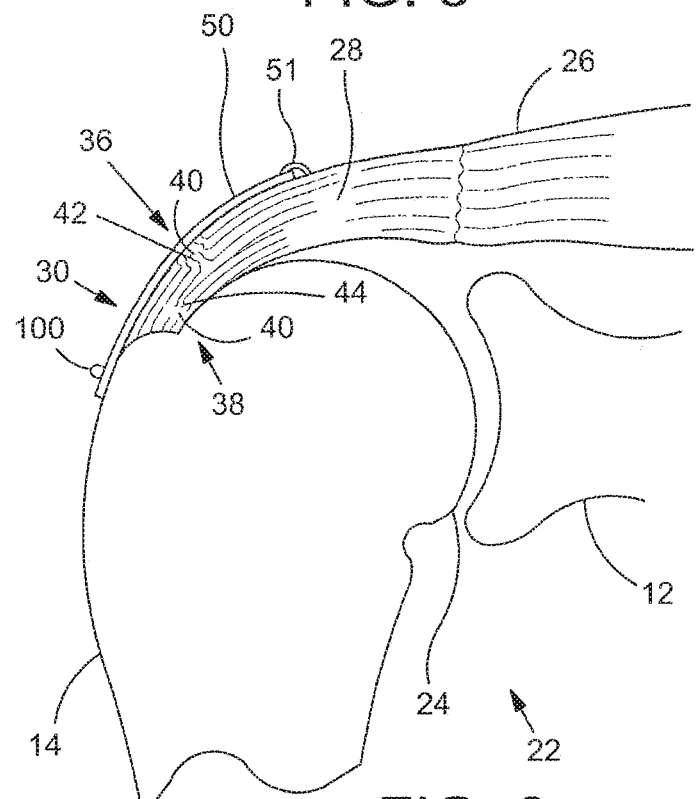
FIG. 6 is a stylized of a shoulder depicting the head of the humerus shown mating with the glenoid fossa of the scapula at a glenohumeral joint and a sheet-like material is affixed to the tendon.

FIG. 6 is a stylized anterior view of a shoulder 22 including a humerus 14 and a scapula 12. In FIG. 6, a head 24 of humerus 14 is shown mating with a glenoid fossa of scapula 12 at a glenohumeral joint. A supraspinatus 26 is also shown in FIG. 6. This muscle, along with others, controls the movement of humerus 14 relative to scapula 12. A distal tendon 28 of supraspinatus 26 meets humerus 14 at an insertion point 30.

As depicted in FIG. 6, distal tendon 28 includes a first damaged portion 36. A number of loose tendon fibers 40 in first damaged portion 36 are visible in FIG. 6. First damaged portion 36 includes a first tear 42 extending partially through distal tendon 28. First tear 42 may therefore be referred to as a partial thickness tear. With reference to FIG. 6, first tear 42 begins on the side of distal tendon 28 facing the subacromial bursa (shown in the previous Figure) and ends midway through distal tendon 28. Accordingly, first tear 42 may be referred to as a bursal side tear.

With reference to FIG. 6, distal tendon 28 includes a second damaged portion 38 located near insertion point 30. As illustrated, second damaged portion 38 of distal tendon 28 has become frayed and a number of loose tendon fibers 40 are visible. Second damaged portion 38 of distal tendon 28 includes second tear 44. Second tear 44 begins on the side of distal tendon 28 facing the center of the humeral head 24. Accordingly, second damaged portion 38 may be referred to as an articular side tear.

FIG. 6 illustrates a sheet-like implant 50 has been placed over the bursal side of distal tendon 28. The sheet-like implant 50 is affixed to distal tendon 28 by a plurality of tendon staples 51. Sheet-like implant 50 is affixed to humerus 14 by a plurality of bone staples 100 in accordance with designs of staples disclosed herein. Sheet-like implant 50 extends over insertion point 30, first tear 42 and second tear 44. Some useful methods in accordance with this detailed description may include placing a tendon repair implant on the bursal side of a tendon regardless of whether the tears being treated are on the bursal side, articular side or within the tendon. In some cases the exact location and nature of the tears being treated may be unknown. A tendon repair implant may be applied to the bursal side of a tendon to treat shoulder pain that is most likely caused by one or more partial thickness tears in the tendon.

Figure 7:
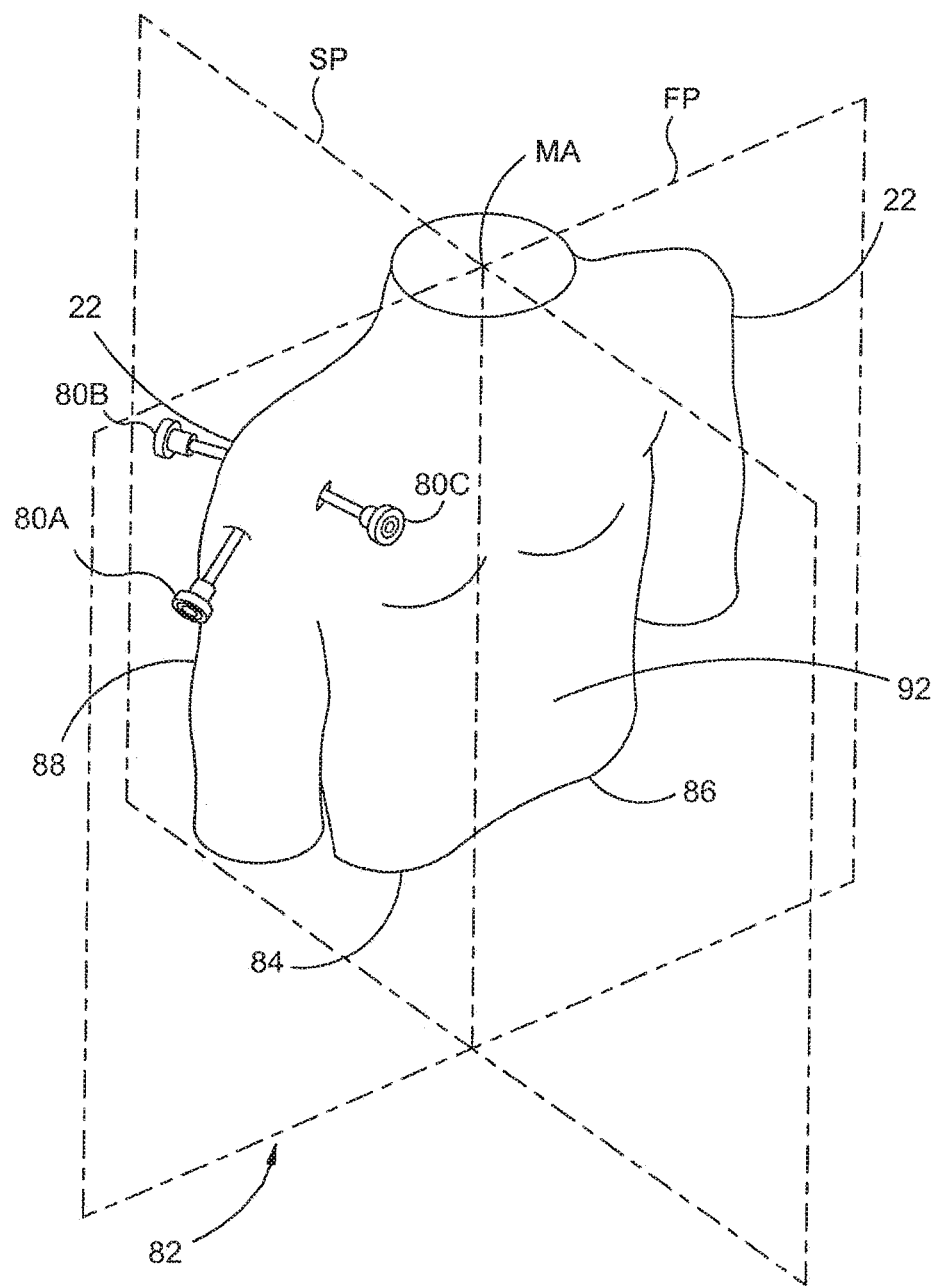
FIG. 7 is a stylized perspective view showing a portion of the body of a human patient divided into quadrants by planes for descriptive purposes herein.

FIG. 7 is a stylized perspective view showing a portion of the body 82 of a human patient 20. Body 82 includes a shoulder 22. In the exemplary embodiment of FIG. 7, a plurality of cannulas are positioned to access a treatment site within shoulder 22. In some cases, shoulder 22 may be inflated by pumping a continuous flow of saline through shoulder 22 to create a cavity proximate the treatment site. The cannulas shown in FIG. 7 include a first cannula 80A, a second cannula 80B and a third cannula 80C.

In FIG. 7, a sagital plane SP and a frontal plane FP are shown intersecting body 82. Sagital plane SP and frontal plane FP intersect one another at a medial axis MA of body 82. With reference to FIG. 7, sagital plane SP bisects body 82 into a right side 84 and a left side 86. Also with reference to FIG. 7, frontal plane FP divides body 82 into an anterior portion 92 and a posterior portion 88. Sagital plane SP and a frontal plane FP are generally perpendicular to one another. These planes and portions are used to describe the procedures used in exemplary embodiments.

First cannula 80A is accessing a treatment site within shoulder 22 using a lateral approach in which first cannula 80A pierces the outer surface of right side 84 of body 82. The term lateral approach could also be used to describe situations in which an instrument pierces the outer surface of left side 86 of body 82. Second cannula 80B is accessing a treatment site within shoulder 22 using a posterior approach in which second cannula 80B pierces the outer surface of posterior portion 88 of body 82. Third cannula 80C is accessing a treatment site within shoulder 22 using an anterior approach in which third cannula 80C pierces the outer surface of anterior portion 92 of body 82.

Figure 8:
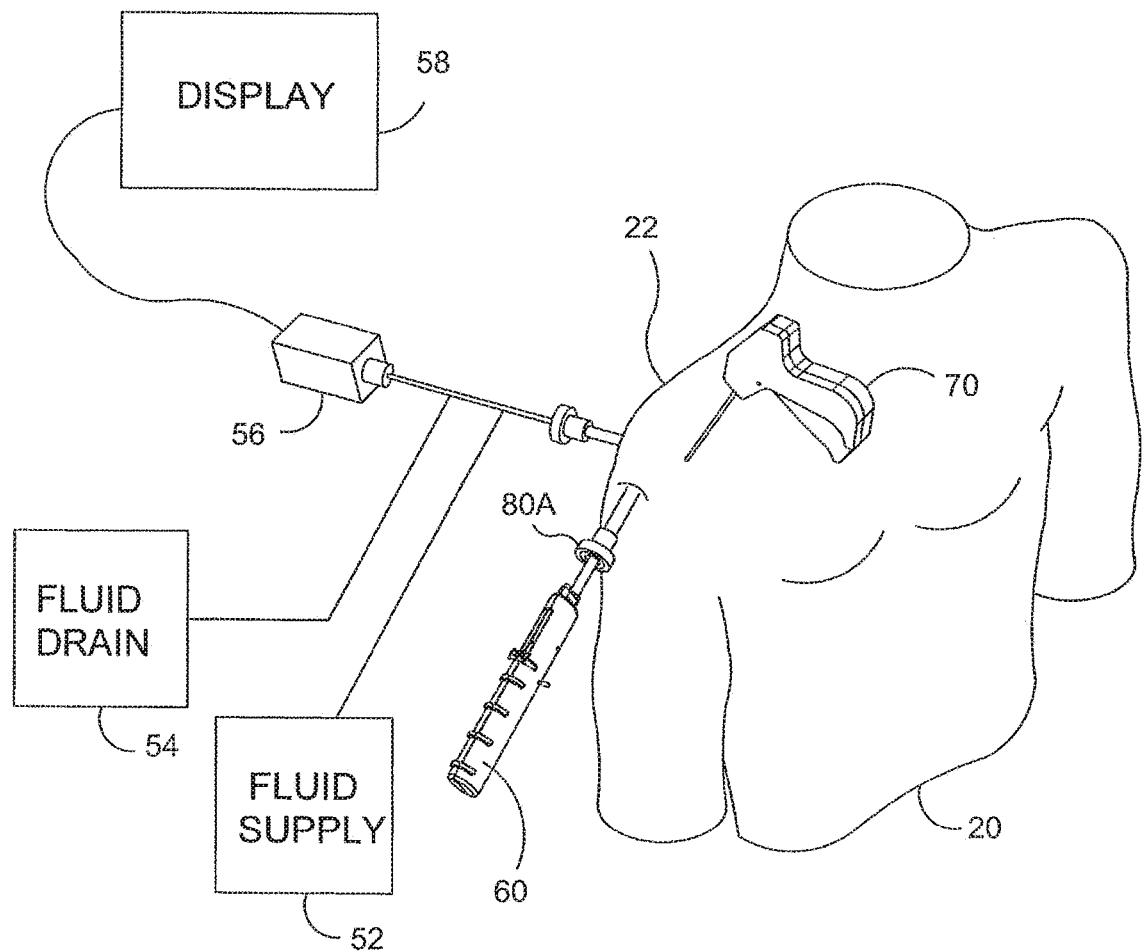
FIG. 8 is a stylized perspective view illustrating an exemplary procedure for arthroscopic treatment of a shoulder of a patient in accordance with one embodiment of the disclosure.

FIG. 8 is a stylized perspective view illustrating an exemplary procedure for treating a shoulder 22 of a patient 20. The procedure illustrated in FIG. 8 may include, for example, fixing tendon repair implants to one or more tendons of shoulder 22. The tendons treated may be torn, partially torn, have internal micro-tears, be untorn, and/or be thinned due to age, injury or overuse.

Shoulder 22 of FIG. 8 has been inflated to create a cavity therein. A fluid supply 52 is pumping a continuous flow of saline into the cavity. This flow of saline exits the cavity via a fluid drain 54. A camera 56 provides images from inside the cavity. The images provided by camera 56 may be viewed on a display 58.

Camera 56 may be used to visually inspect the tendons of shoulder 22 for damage. A tendon repair implant in accordance with this disclosure may be affixed to a bursal surface of the tendon regardless of whether there are visible signs of tendon damage. Applicants believe that the methods and apparatus of the present application and related devices may provide very beneficial therapeutic effect on a patient experiencing joint pain believed to be caused by internal microtears, but having no clear signs of tendon tears. By applying a tendon repair implant early before a full tear or other injury develops, the implant may cause the tendon to thicken and/or at least partially repair itself, thereby avoiding more extensive joint damage, pain, and the need for more extensive joint repair surgery.

An implant delivery system 60 can be seen extending from shoulder 22 in FIG. 8. Implant delivery system 60 is extending through a first cannula 80A. In certain embodiments, first cannula 80A can access a treatment site within shoulder 22 using a lateral approach in which first cannula 80A pierces the outer surface of a right side of the patient's body. In some cases a physician may choose not to use a cannula in conjunction with implant delivery system 60. When that is the case, the implant delivery system may be advanced through tissue. Implant delivery system 60 comprises a sheath that is affixed to a handle. The sheath defines a lumen and a distal opening fluidly communicating with the lumen. In the embodiment of FIG. 8, the distal opening of the sheath has been placed in fluid communication with the cavity created in shoulder 22.

A tendon repair implant is at least partially disposed in the lumen defined by the sheath of implant delivery system 60. Implant delivery system 60 can be used to place the tendon repair implant inside shoulder 22. In some embodiments, the tendon repair implant is folded into a compact configuration when inside the lumen of the sheath. When this is the case, implant delivery system 60 may be used to unfold the tendon repair implant into an expanded shape. Additionally, implant delivery system 60 can be used to hold the tendon repair implant against the tendon.

The tendon repair implant may be affixed to the tendon while it is held against the tendon by implant delivery system 60. Various attachment elements may be used to fix the tendon-repair implant to the tendon. Examples of attachment elements that may be suitable in some applications include sutures, tissue anchors, bone anchors, and staples. In the exemplary embodiment of FIG. 8, the shaft of a fixation tool 70 is shown extending into shoulder 22. In one exemplary embodiment, fixation tool 70 is capable of fixing the tendon repair implant to the tendon and bone with one or more staples of the present disclosure while the tendon repair implant may held against the tendon by implant delivery system 60.

Figure 9:
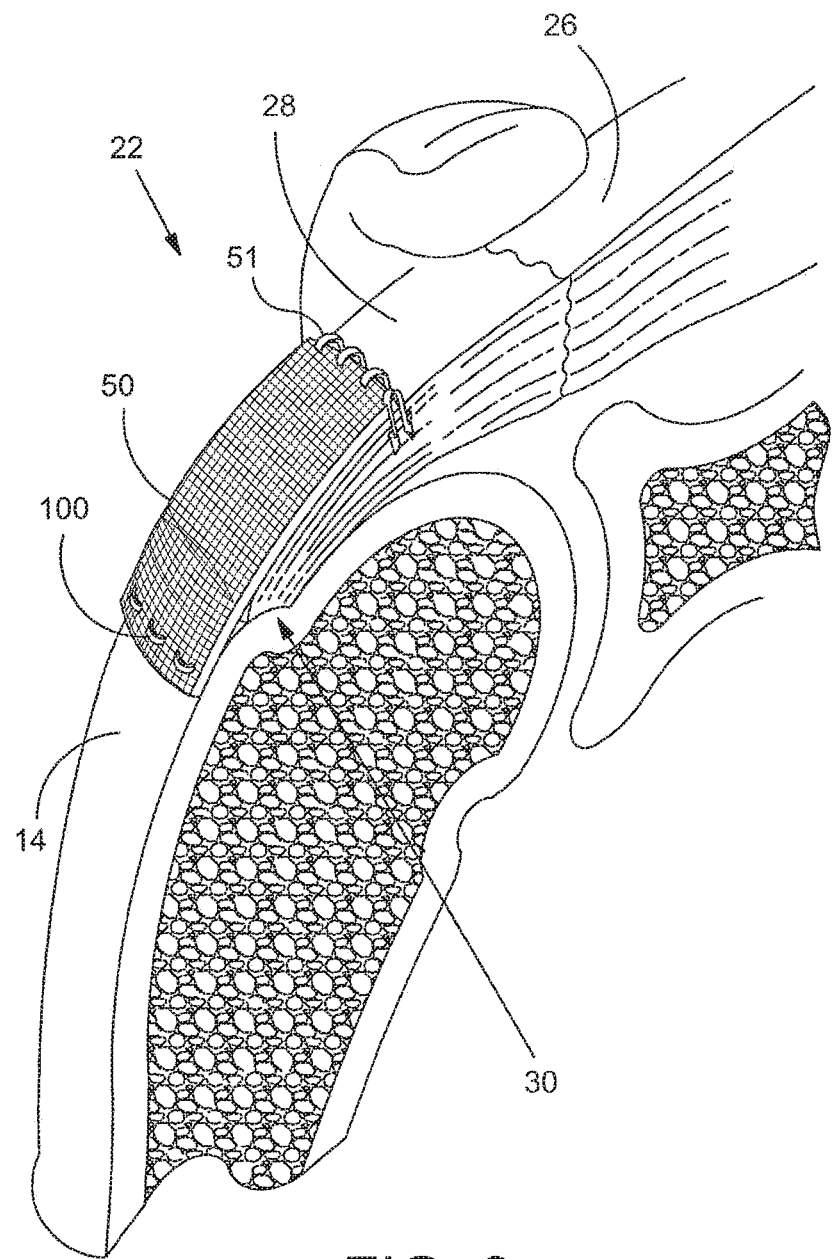
FIG. 9 is a stylized perspective view of a shoulder including a supraspinatus having a distal tendon with a sheet-like material affixed thereto.

FIG. 9 is a stylized perspective view of a shoulder 22 including a supraspinatus 26 having a distal tendon 28. With reference to FIG. 9, a tendon repair implant 50 has been affixed to a surface of distal tendon 28. Tendon repair implant 50 may comprise, for example, various sheet-like structures without deviating from the spirit and scope of the present detailed description. In some useful embodiments, the sheet-like structure may comprise a plurality of fibers. The fibers may be interlinked with one another. When this is the case, the sheet-like structure may comprise a plurality of apertures comprising the interstitial spaces between fibers. Various processes may be used to interlink the fibers with one another. Examples of processes that may be suitable in some applications including weaving, knitting, and braiding. In some embodiments, the sheet-like structure may comprise a laminate including multiple layers of film with each layer of film defining a plurality of micro-machined or formed holes. The sheet-like structure of the tendon repair implant may also comprise a reconstituted collagen material having a porous structure. Additionally, the sheet-like structure of the tendon repair implant may also comprise a plurality of electro-spun nanofiber filaments forming a composite sheet. Additionally, the sheet-like structure may comprise a synthetic sponge material that defines a plurality of pores. The sheet-like structure may also comprise a reticulated foam material. Reticulated foam materials that may be suitable in some applications are available from Biomerix Corporation of Fremont, Calif. which identifies these materials using the trademark BIOMATERIAL™. The sheet-like structure may be circular, oval, oblong, square, rectangular, or other shape configured to suit the target anatomy.

Various attachment elements may be used to fix tendon repair implant 50 to distal tendon 28 without deviating from the spirit and scope of this detailed description. Examples of attachment elements that may be suitable in some applications include sutures, tissue anchors, bone anchors, and staples. In the embodiment of FIG. 9, sheet-like implant 50 is affixed to distal tendon 28 by a plurality of tendon staples 51. Sheet-like implant 50 is affixed to humerus 14 by a plurality of bone staples 100 as described with respect to the exemplary embodiment of FIG. 1 and detailed throughout this disclosure.

In some exemplary methods, a plurality of staples may be applied using a fixation tool. After the staples are applied, the fixation tool may be withdrawn from the body of the patient. Distal tendon 28 meets humerus 14 at an insertion point 30. With reference to FIG. 9, it will be appreciated that sheet-like implant 50 extends over insertion point 30. Tendon repair implant may be applied to distal tendon 28, for example, using the procedure illustrated in the previous figures. In various embodiments, staples may straddle the perimeter edge of the sheet-like implant (as shown in FIG. 9), may be applied adjacent to the perimeter, and/or be applied to a central region of the implant. In some embodiments, the staples may be used to attach the implant to soft tissue and/or to bone.

Staples or fasteners 100, as exemplified in FIG. 1 and described and illustrated herein can be used to attach tissue and implants to bone. In at least some embodiments, the staple is generally flexible and includes areas of relative lateral weakness on the trunks and can further include an increase in flexibility at the transition from the trunk to the non-trunk portion of the arm or the transition from the trunk to the bridge. As described above, these areas of increased flexibility provide improved staple retention as these portions allow flexing and bending in response to increasing pullout forces. With this flexibility, the fasteners cannot be pounded or driven into bone or other tissue as a conventional hard staple would be driven into paper, wood, tissue or bone. Therefore, for application of the staple of the present disclosure to affixing tissue or implants to bone, the staple is generally included in a kit that also includes a staple delivery device 200 and a pilot hole forming trocar assembly 300, as schematically illustrated in FIGS. 10A and 10B, respectively.

In general, the staple delivery device 200 can include a handle assembly 201 and a barrel assembly 205. The handle assembly 201 includes a trigger 203 that is operatively coupled to mechanisms in the barrel assembly 205 to deploy a staple of the present disclosure in bone. The staple delivery device 200 can be used in conjunction with the pilot hole forming trocar assembly 300 of FIG. 10B.

Figure 10B:
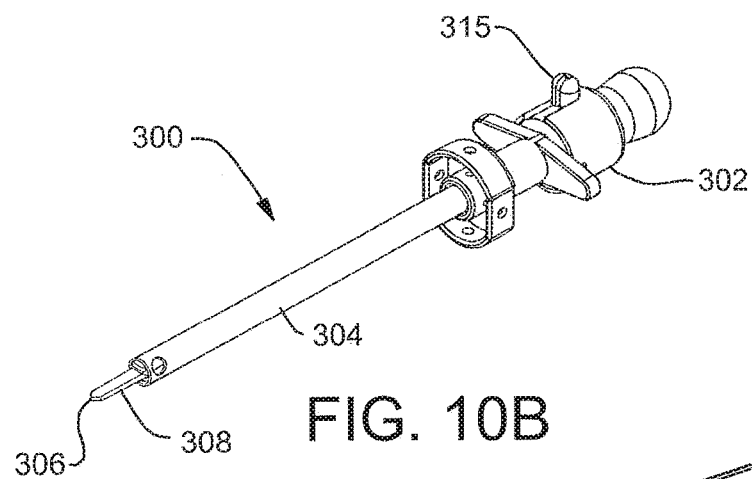
FIG. 10B is a simplified perspective view of a trocar assembly, including a trocar disposed within a guide sheath assembly for creating pilot holes and retaining the sheath within the formed pilot holes for delivery of a tissue fastener or staple by a device such as that depicted in FIG. 10A.
Figure 10A:
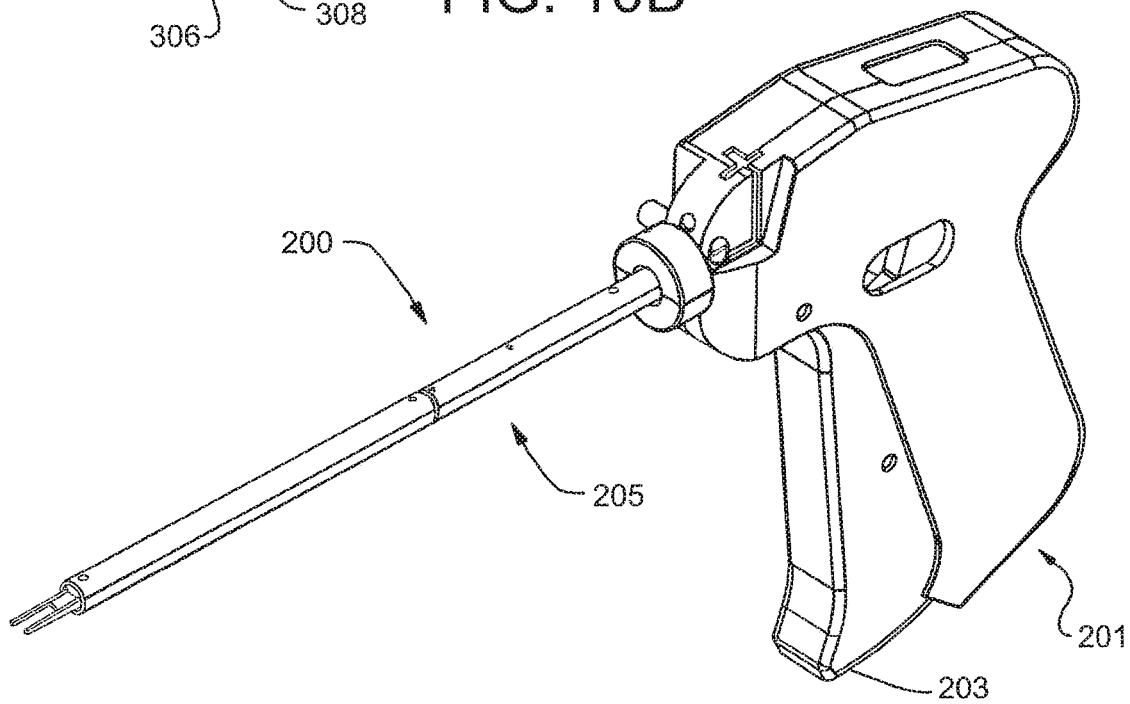
FIG. 10A is a simplified perspective view of a tissue fastener or staple delivery device in accordance with the present disclosure.

The pilot hole forming trocar assembly 300, illustrated generally in FIG. 10B includes a trocar 302 and a position retention sleeve 304. The trocar 302 is releasably coupled to the position retention sleeve 304 and slides in keyed arrangement within the sleeve 304 when uncoupled. The trocar 302 includes a distal portion having a retractable blade 306 and a pair of pilot hole forming spikes 308 extending distally from the trocar shaft. The retractable blade 306 is useful in inserting the assembly through an incision. The retractable blade 306 can be retracted in this embodiment by activating release button 315 which causes a spring (not shown) to pull the retractable blade 306 into the shaft of the trocar within the position retention sleeve 304. In this the position, the pilot hole forming spikes remain extended from the shaft. In some embodiments the retractable blade 306 can be omitted if the pilot hole forming trocar assembly is to be inserted into an incision that already has a cannula extending therethrough to provide an instrument path.

Figure 11B:
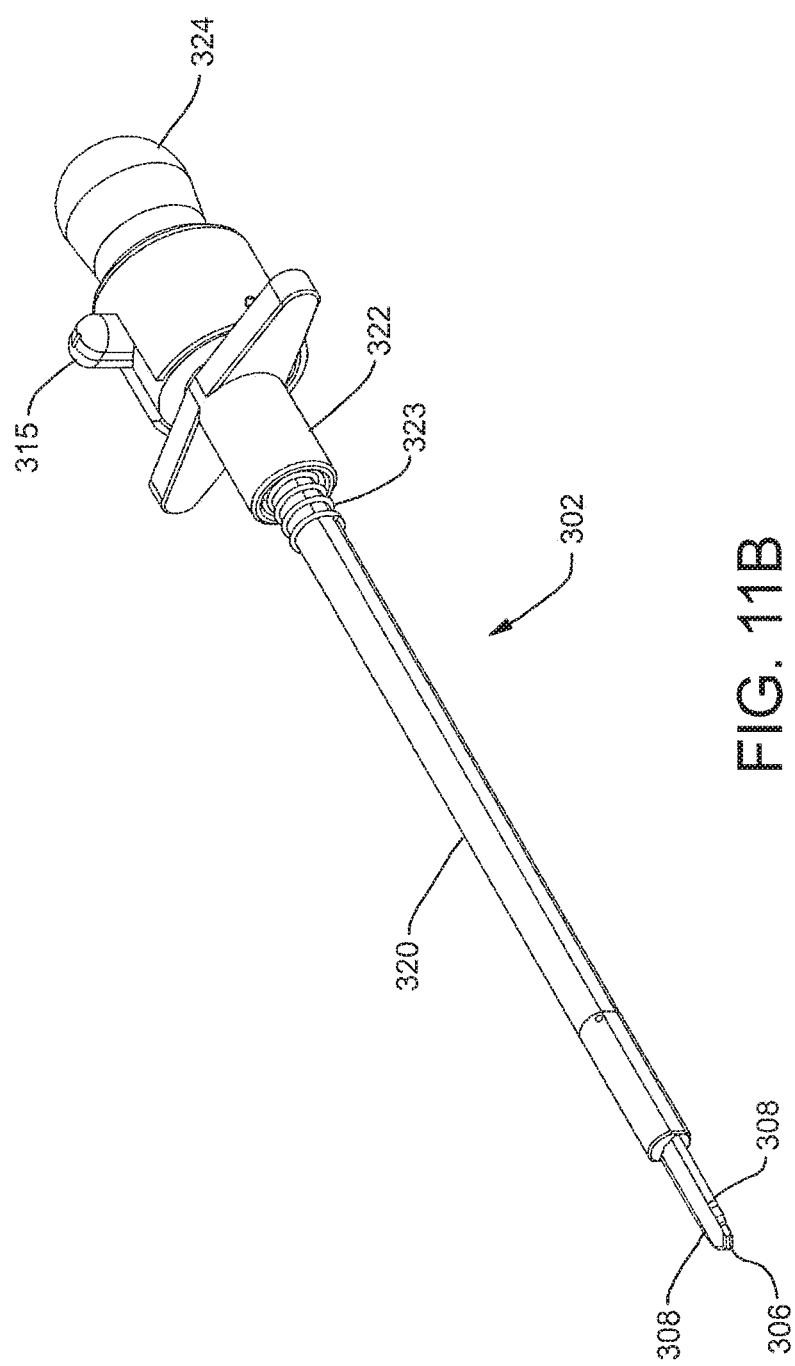
FIG. 11B is a perspective view of the trocar of FIG. 10B as removed from the sheath assembly.

Referring to FIGS. 11A-11C, details of the elements of one embodiment of a pilot hole forming trocar assembly 300 are illustrated. The pilot hole forming trocar assembly is used to created pilot holes in a bone for subsequent placement of a staple or fastener, such as staple 100 of FIG. 1. Further, the pilot hole forming trocar assembly includes a means for retaining instrument position with respect to the pilot holes when the trocar is removed so that a staple delivery device 200 can be inserted and the staple be in alignment with the already formed pilot holes. This prevents the time and difficulty associated with finding the pilot holes with the staple, which in fact may not be possible for many practitioners.

As previously stated, a pilot hole forming trocar assembly 300 can include a trocar 302 and a position retention sleeve 304. One embodiment of a position retention sleeve 304 is illustrated in FIG. 11A. The position retention sleeve 304 includes a shaft 311 having a lumen 310 extending therethrough. The lumen 310 is sized to receive the trocar 302 when used to form pilot holes. The lumen 310 is also sized to receive a staple delivery device 200 when used to position a staple in a pilot hole formed in bone. The lumen is shaped or keyed to cooperate with either of these instruments or other instruments so that relative rotational position of the trocar 302 or staple delivery device 200 is fixed when slidably positioned in the position retention sleeve. An opening or window 313 may be included near the distal end of the position retention sleeve to allow viewing of devices inserted therein.

Position retention members 314 extend distally from the shaft 311. As detailed in FIG. 11C, the position retention members can be included on an insert 312 that is affixed proximate the distal end of the shaft 311. Alternatively, the position retention members can be integral to the shaft 311. The position retention members are sized and designed to extend into pilot holes as they are foamed by the trocar 302 described below. When the trocar 302 is removed, the position retention members 314, along with the sleeve 311 remain in position to provide a guide for the staple delivery device 200 to be inserted into proper position and position a staple 100 in the pilot holes. As depicted, the position retention members 314 can include longitudinally extending semi-cylindrical projections. In the disclosed embodiment, the pilot hole forming spikes 308 of the trocar 302 slide within the partial lumens of the position retention members 314. This design can provide support for the spikes as they are pounded into bone and can also allow the position retention members to readily slide into pilot holes formed by the spikes 308.

A more detailed depiction of one alternative embodiment of a trocar 302 is included in FIG. 11B. The trocar includes a shaft 320 having at its proximal end a knob 324 that can be used to pound or push the trocar 302 into bone. The trocar can further include a collar 322 which can be used to releasable engage the position retention sleeve 304 when the two are mated for forming pilot holes. A spring 323 can be included which causes or aids the retraction of the trocar when it is released from the position retention sleeve.

As previously disclosed, the distal end of the trocar 302 includes two pilot hole forming spikes 308 extending from shaft 320. A retractable blade 306 is positioned between the spikes 308. In use, the blade 306 is retracted prior to the spikes 308 being used to form pilot holes in bone.

Figure 12:
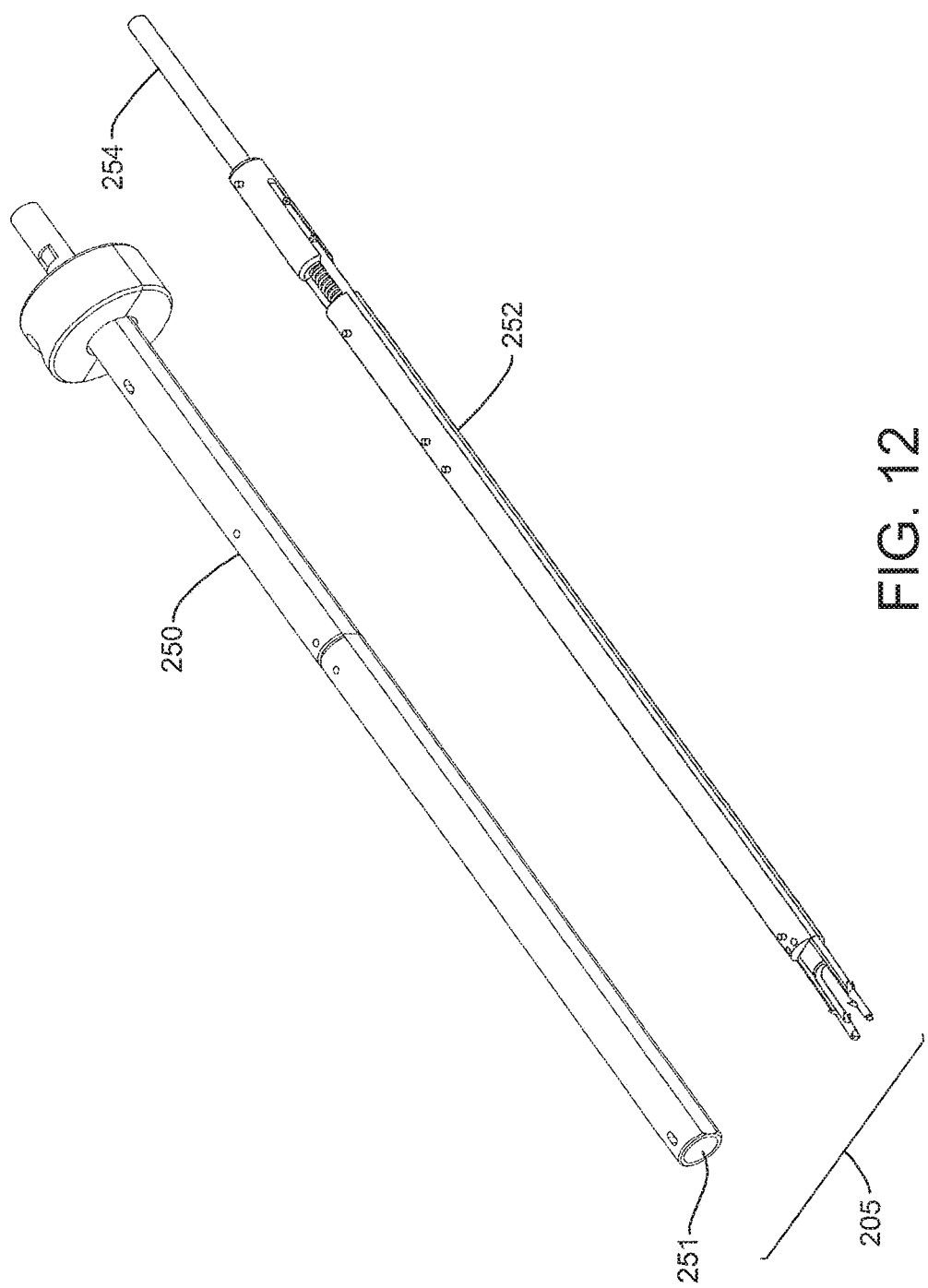
FIG. 12 is a perspective view depicting the sheath and staple pusher assemblies of a staple delivery device in one embodiment of the disclosure.

Now referring to FIG. 12, the two main components of one embodiment of the barrel assembly 205 are illustrated. The barrel assembly includes an outer sleeve 250 having a lumen 251 extending therethrough. The outer sleeve 250 is secured to the handle assembly 201 in fixed relationship when the staple delivery device 200 is assembled. A staple delivery assembly 252 is slidably disposed in the lumen 251 and includes a proximal end 254 extending beyond the proximal end of the sleeve 250. The proximal end 254 of the staple delivery assembly 252 operatively interacts with trigger assembly 203 when the barrel 205 is mounted on the handle assembly 201. In the embodiment of FIG. 12, the outer surface of the sleeve 250 is shaped so as to be rotationally keyed and sized for desired fitting within the position retention sleeve 304. The sleeve 250 includes a flat surface 257 keyed to fit within a flat surface on the interior of the position retention sleeve 304.

Figure 13:
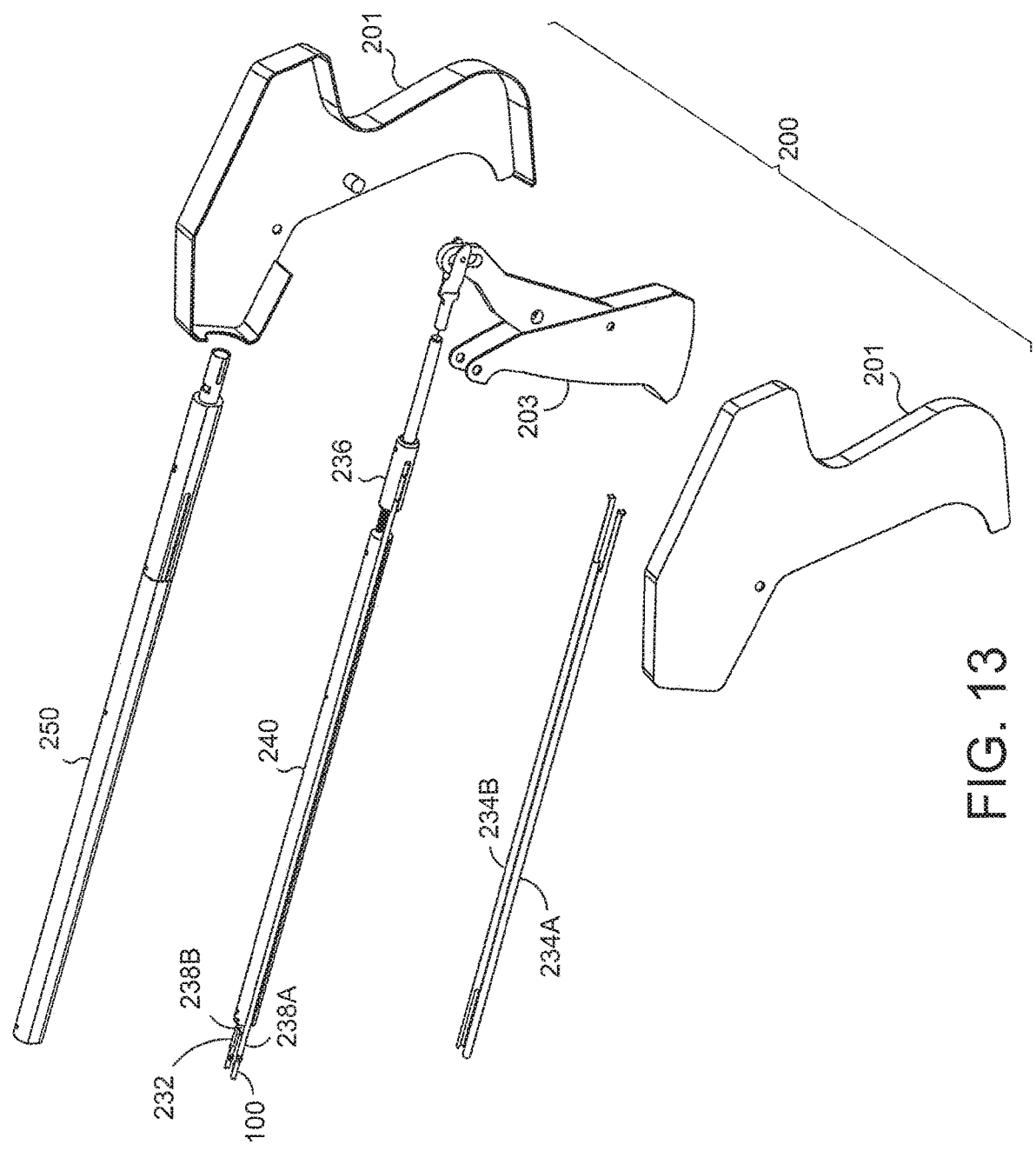
FIG. 13 is a simplified exploded view of the tissue fastener or staple delivery device of FIG. 10A depicting additional features thereof.

The operation of some embodiments of the staple delivery device 200 is further understood with reference to FIG. 13. FIG. 13 is an exploded view showing the staple delivery device 200 that may be used in conjunction with a staple 100 and the above described pilot hole forming trocar 300. The handle assembly 201 and barrel assembly 205 are shown with the barrel assembly including both the sleeve 250 and staple delivery assembly 252 included. Staple delivery assembly 252 includes a fork 232, a shaft 240, and two staple setting rods 234. Staple setting rods 234 include a first staple setting rod 234A and a second staple setting rod 234B. Both staple setting rods 234 are affixed to a rod coupler 236 of staple delivery assembly 252 in the embodiment of FIG. 13. When the barrel 205 is in an assembled state, first staple setting rod 234A and second staple setting rod 234B can extend through two grooves defined by shaft 240. Each groove is dimensioned so that a staple setting rod can be partially disposed therein while the sleeve 250 surrounds the staple setting rods 234 and shaft 240.

When staple delivery device 200 is in an assembled state, staple 100 may be carried by a first stake 238A and a second stake 238B of fork 232. As previously described with respect to FIG. 1, staple 100 can include a first aim 102A, a second arm 102B, and a bridge 104 extending from the proximal end of first arm 102A to the proximal end of second arm 102B. The distal end of the non-trunk portion of first arm 102A abuts the proximal end of a first trunk 106A. Similarly, the distal end of the non-trunk portion of second arm 102B abuts the proximal end of a second trunk 106B.

Now referring to FIGS. 14-17, details of some exemplary embodiments and features of the staple delivery assembly 252 and the mounting and delivery of a staple 100 are illustrated. Various aspects of these elements may be included in embodiments of the overall staple delivery device 200 of this disclosure.

Figure 14:
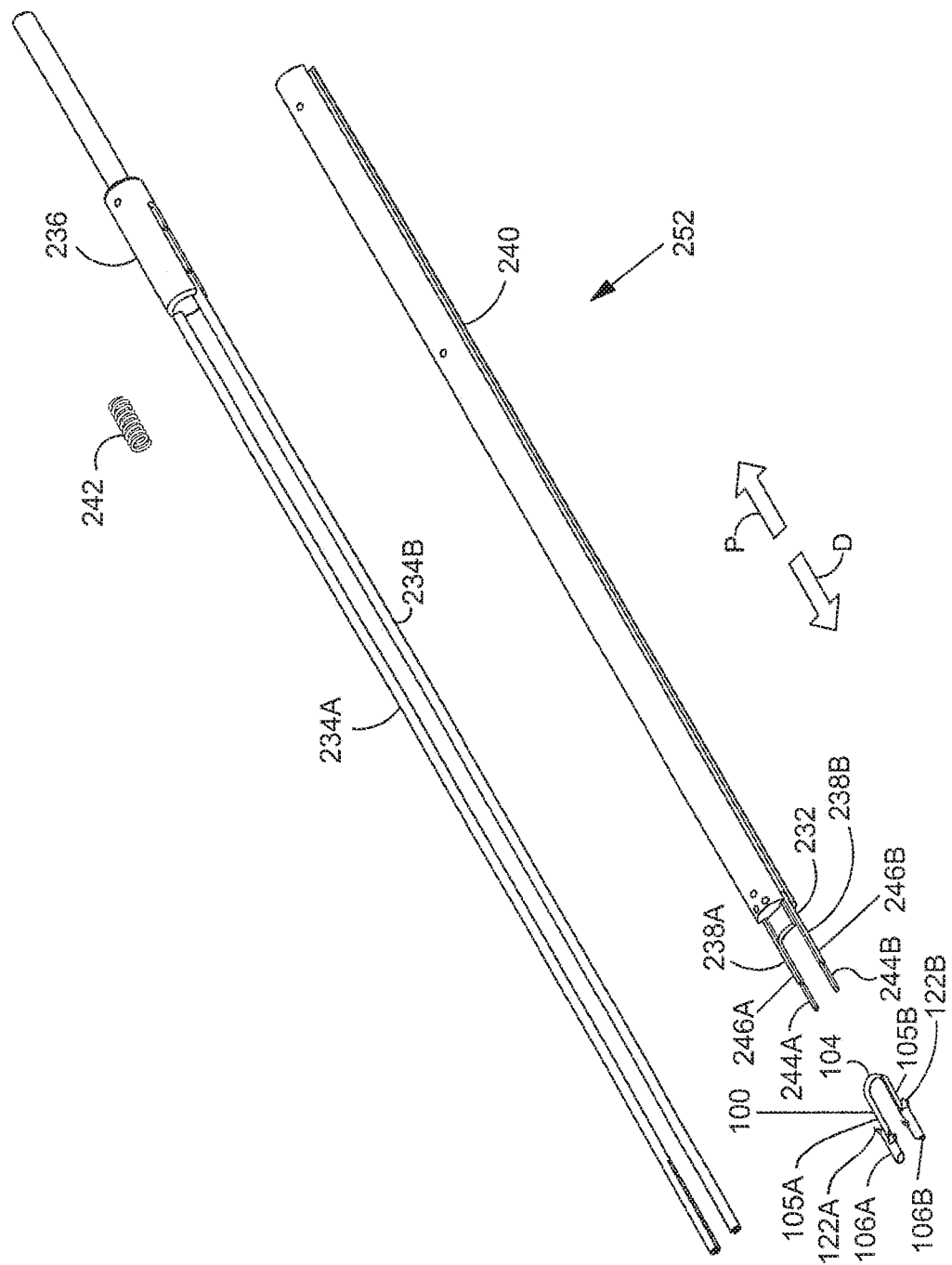
FIG. 14 depicts further features of the staple pusher assembly of FIG. 13.
Figure 15:
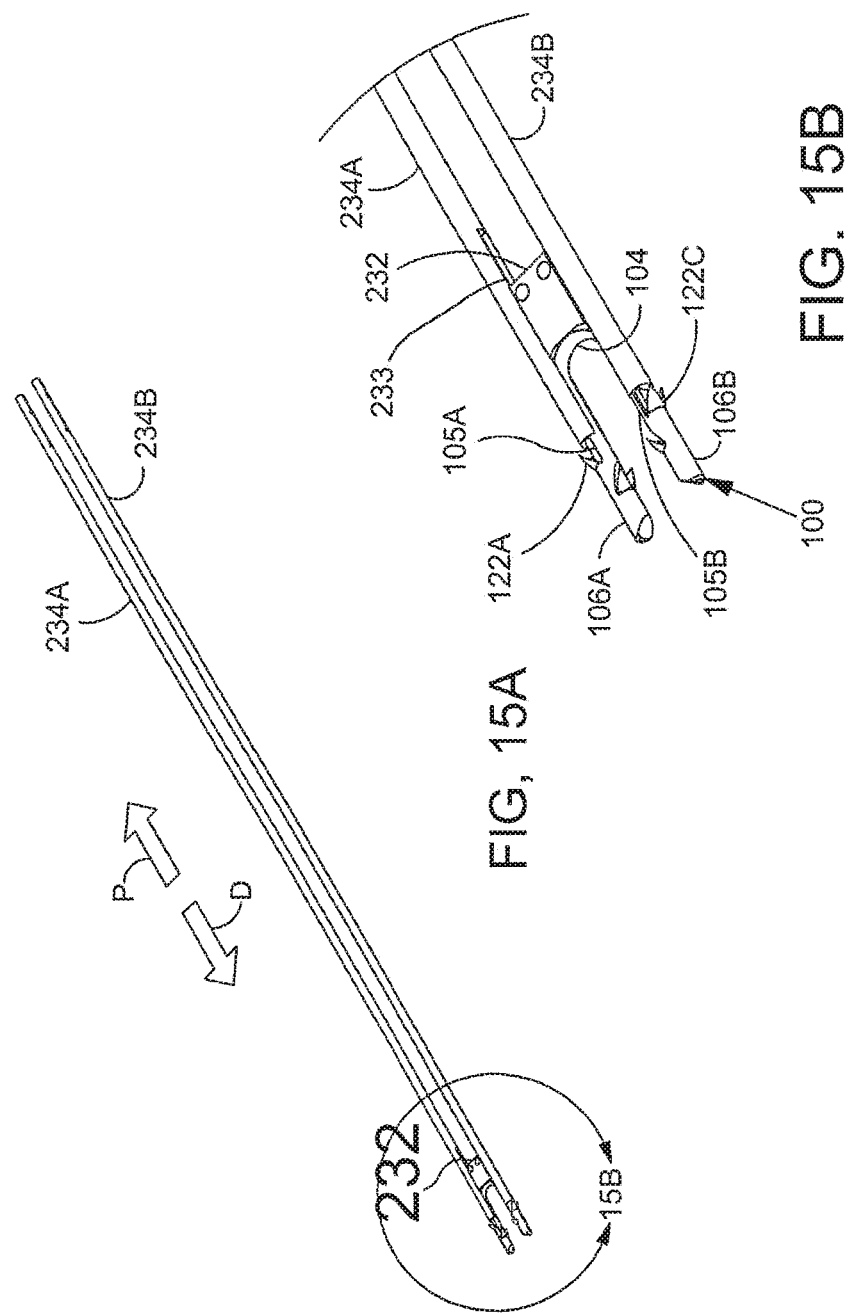
FIGS. 15A and 15B illustrate the features of the distal portion of the staple pusher assembly of FIG. 13 with a staple mounted thereon in accordance with one embodiment of the disclosure.
Figure 16:
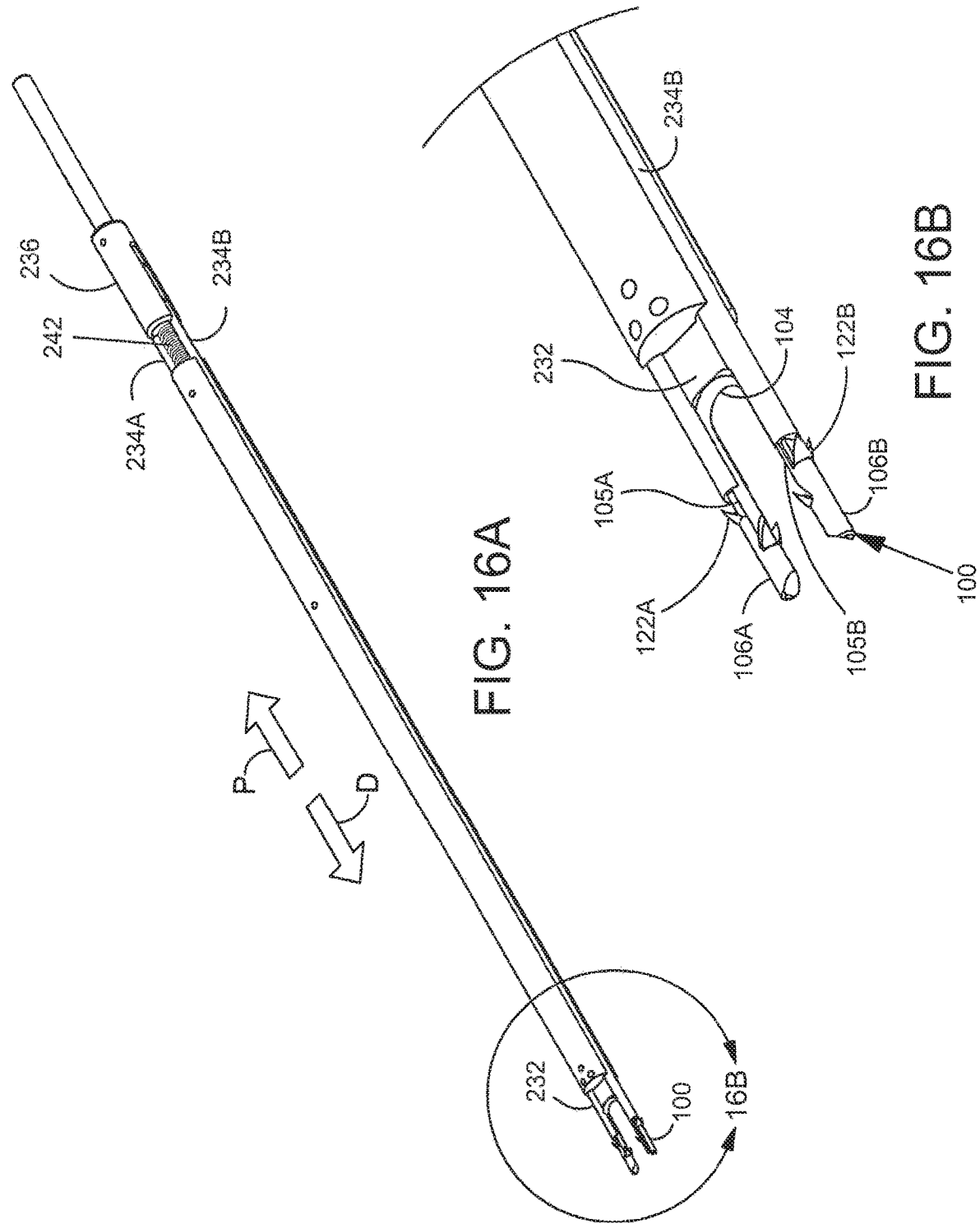
FIGS. 16A and 16B further illustrate the staple pusher assembly in one embodiment of the disclosure.

The components of a staple delivery assembly 252 are illustrated in FIG. 14. First stake 238A and second stake 238B of fork 232 can be seen extending distally away from a distal end of shaft 240 in FIG. 14. The distal direction is indicated with an arrow D. In the embodiment of FIG. 14, first stake 238A includes a distal portion 244A and a proximal portion 246A. Second stake 238B includes a distal portion 244B and a proximal portion 246B. In some useful embodiments, each distal portion 244 is dimensioned to extend into a cavity defined by a staple, such as cavity 128A, 128B of staple 100 in FIG. 1. When this is the case, the staple may be supported by each distal portion 244 that extends into a passage defined by the staple. In this way, fork 232 may be used to carry a staple. Staple 100 is illustrated proximate the distal end of shaft 240 to show the staple features relative to the staple delivery assembly 252 prior to mounting the staple thereon. Staple setting rods 234 are illustrated as attached to rod coupler 236 and it can be seen how these rods can slidably engage the channels running longitudinally on shaft 240. Spring 242 is also depicted.

In FIGS. 15A and 15B, the staple setting rods 234, fork 232 and staple 100 are shown as initially assembled in one embodiment, prior to adding shaft 240. In particular, FIG. 15B depicts fork 232 slidably disposed in channels 233. It further shows the way in which staple settings rods are disposed within cavities in the staple and the distal ends of the staple setting rods 234 extend to abut a proximal surface of the staple, in this embodiment the proximal surface is the proximal end of the trunk. In some useful methods, staple setting rods 234 are moved distally to apply pushing forces to one or more proximal surfaces of staple 100. These pushing forces may be used, for example, to urge first projection 122A and third projection 122C into orientations that lock staple 100 into a target tissue. For example, first projection 122A and third projection 122C may be rotated so that these projections engage the target tissue. When this is the case, tension extending through bridge 104 of staple 100 may keep first projection 122A and third projection 122C in the rotated position. Also when this is the case, the projections may inhibit staple pullout.

In FIGS. 16A and 16B, the initial assembly of FIG. 15A is shown with the shaft 240 in position, along with the staple setting rods affixed to the rod coupler 236 and the spring positioned between the rod coupler 236 and the proximal end of the shaft 240. The spring 242 of staple delivery assembly 252 may be compressed as staple setting rods 234 are moved distally to urge first projection 122A and third projection 122C into orientations that lock staple 100 into a target tissue. After staple 100 has been set, spring 242 may urge staple setting rods 234 proximally toward a starting position. When staple delivery assembly 252 is in an assembled state, a distal end of spring 242 is seated against a proximal end of shaft 240 and a proximal end of spring 242 is seated against the distal end of rod coupler 236. Spring 242 may deflect as staple setting rods 234 are moved proximally and distally relative to shaft 140. Distal and proximal directions are indicated with arrows labeled D and P.

Figure 17:
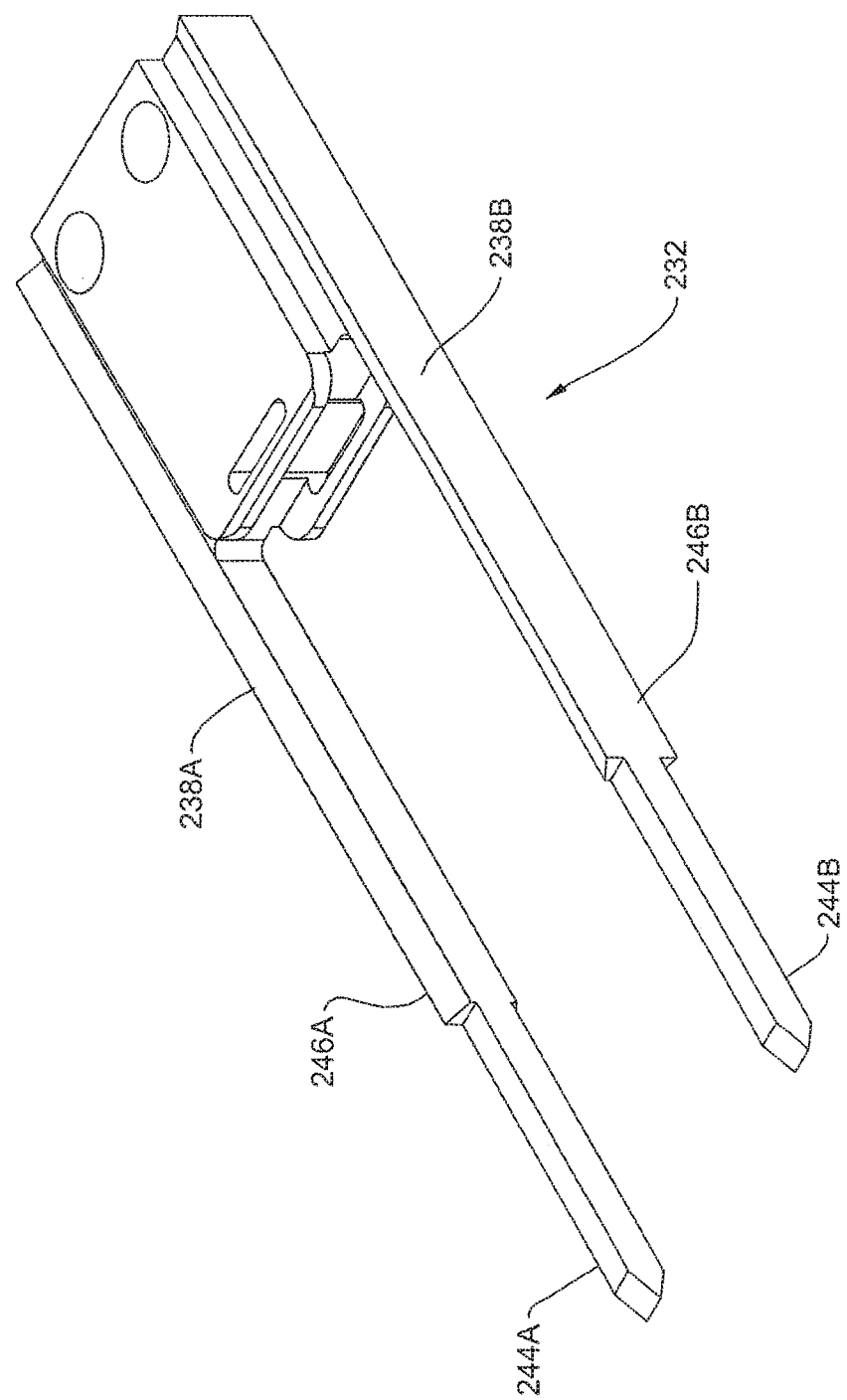
FIG. 17 is a more detailed perspective view of the distal portion of the staple pusher assembly illustrating stakes that mate with the staple in one embodiment of the disclosure.

FIG. 17 is a perspective view further illustrating fork 232 shown more generally in the previous figures. Fork 232 includes a first stake 238A and a second stake 238B. First stake 238A includes a distal portion 244A and a proximal portion 246A. Second stake 238B includes a distal portion 244B and a proximal portion 246B. The proximal portion 246 of each stake 238 has generally dovetail-shaped lateral cross-section. In some useful embodiments, each proximal portion 246 is dimensioned to be received in a dovetail-shaped slot defined by a staple setting rod 234. When this is the case, the staple setting rod and the fork are coupled to each other with a single degree of freedom for relative movement such that the staple setting rod can slide in distal and proximal directions relative to the fork, as previously described.

As depicted in the prior drawings, the manner in which a staple 100, a first staple setting rod 234A and a second staple setting rod 234B engage fork 232 allows placement of the staple with active engagement and retention in the tissue or bone. Each staple setting rod 234 is disposed in sliding engagement with fork 232. A distal end of each staple setting rod 234 is disposed near a staple 100 that is carried by fork 232.

Staple 100 is designed to cooperatively engage the fork and staple setting rods when mounted thereon for placement in bone. As previously described, the staple 100 can include a first arm 102A, a second arm 102B, and a bridge 104 extending from the proximal end of first arm 102A to the proximal end of second arm 102B. At least the distal portion of first arm 102A is a trunk that abuts a non-trunk portion of first arm 102A or the bridge 104. The same is true of second arm 102B. First trunk 106A and second trunk 106B define a first cavity 128A and a second cavity 128B, respectively.

Fork 132 includes a first stake 238A and a second stake 238B. A distal portion 244A of first stake 238A of fork 232 can be seen extending into first cavity 128A defined by first trunk 106A of staple 100. A distal portion 244B of second stake 238B of fork 232 extends into second cavity 128B defined by second trunk 106B of staple 100.

The proximal portion of each stake 238 has a generally dovetail-shaped lateral cross-section. Proximal portion 246A of first stake 238A is slidingly received in a dovetail-shaped slot defined by first staple setting rod 234A. Similarly, proximal portion 246B of second stake 238B is slidingly received in a dovetail-shaped slot defined by second staple setting rod 234B. Accordingly, each staple setting rod is coupled to fork 232 with a single degree of freedom for relative movement such that the staple setting rod can slide in distal and proximal directions relative to the fork.

The staple setting rods 234 may be moved so that the distal end of each staple setting rod abuts a proximal surface of staple 100. Each staple setting rod may apply pushing forces to one or more proximal surfaces of staple 100. Forces applied by the staple setting rods may be used to urge first projection 122A and third projection 122C into orientations that lock staple 100 into a target tissue. For example, first projection 122A and third projection 122C may be rotated so that these projections engage the target tissue. When this is the case, tension extending through bridge 104 of staple 100 may keep first projection 122A and third projection 122C in the rotated position in which the projections inhibit staple pullout.

As assembled, the distal end of the staple delivery assembly 252 is enclosed by the end of the sheath 250. Initial movement of the trigger causes the stable delivery assembly to extend beyond the distal end of the sheath 150 which inserts the staple 100 into pilot holes in the bone. Continue movement of the trigger then forces the staple setting rods distally to set the staples in engagement with the bone.

Figure 18A:
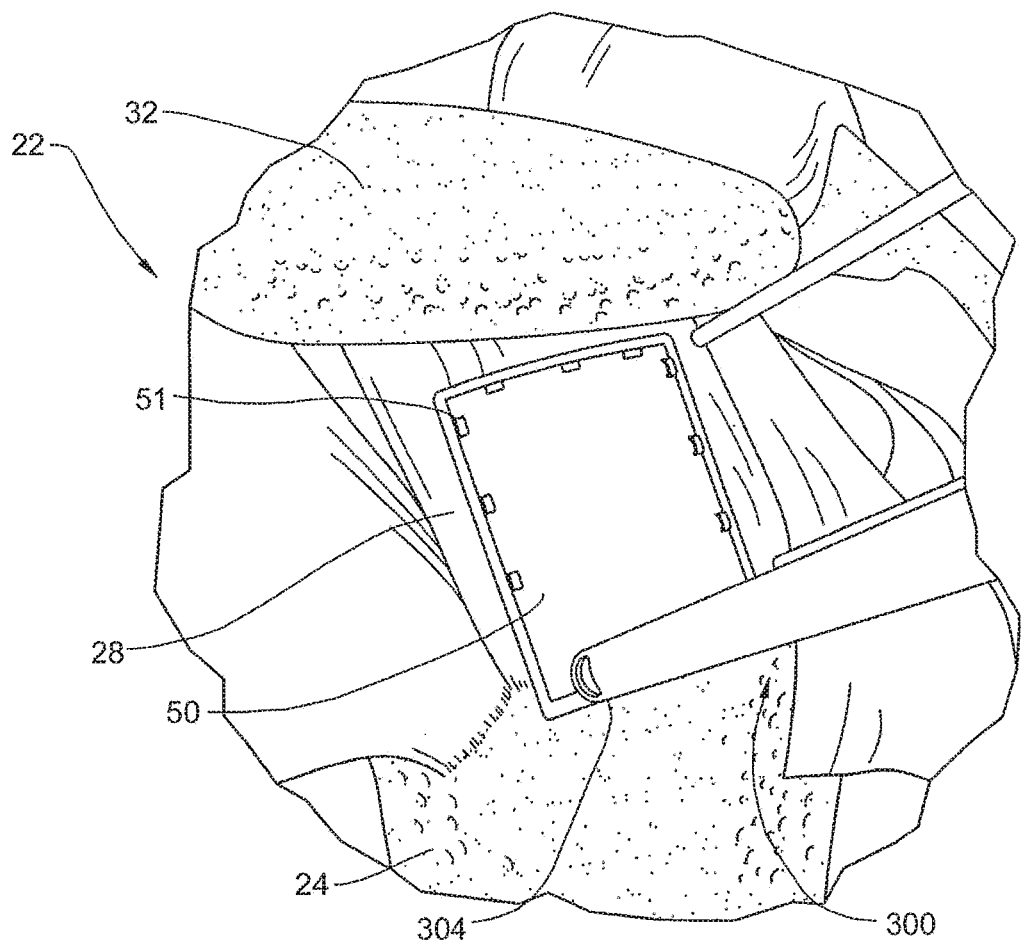
FIG. 18A is simplified perspective view of a shoulder having an implant affixed to the tendon and depicting the first step in a method of delivering fasteners to affix the implant to bone of the humeral head in accordance with one method of the disclosure.

The process of forming pilot holes and delivery staples of the present disclosure to bone is described with respect to FIGS. 18A-18F which depict the various steps in affixing an implant 50 to bone with staples or fasteners of the present disclosure. FIG. 18A schematically depicts a shoulder 22 of a patient 20 having an implant 50 positioned over a supraspinitus tendon 28. The implant is partially affixed to the tendon 28 with fasteners 51 and extends laterally to and over the insertion point of the tendon to the humeral head 24. As depicted, the implant 50 is not yet affixed to the humeral head 24. A distal portion of a pilot hole forming trocar assembly 300, in particular the position retention sleeve 304, is disposed over a desired location near the lateral edge of the implant 50 where it overlies the humeral head 24. It is noted the FIG. 18A is a depiction with all overlying tissue removed from the shoulder 22 to clearly show the location of the entire implant 50 on the supraspinitus tendon 28. This view is not possible during actual arthroscopic procedures in which the fasteners and instruments of the present disclosure can be used, however the depiction provides a clear understanding of the placement of an implant and the use of fasteners disclosed herein. In actual use the surgeon will have a side view from a viewing scope (not shown) of a small space created by inflating the area with fluid and clearing necessary obstructions from the implant area.

Figure 18B:
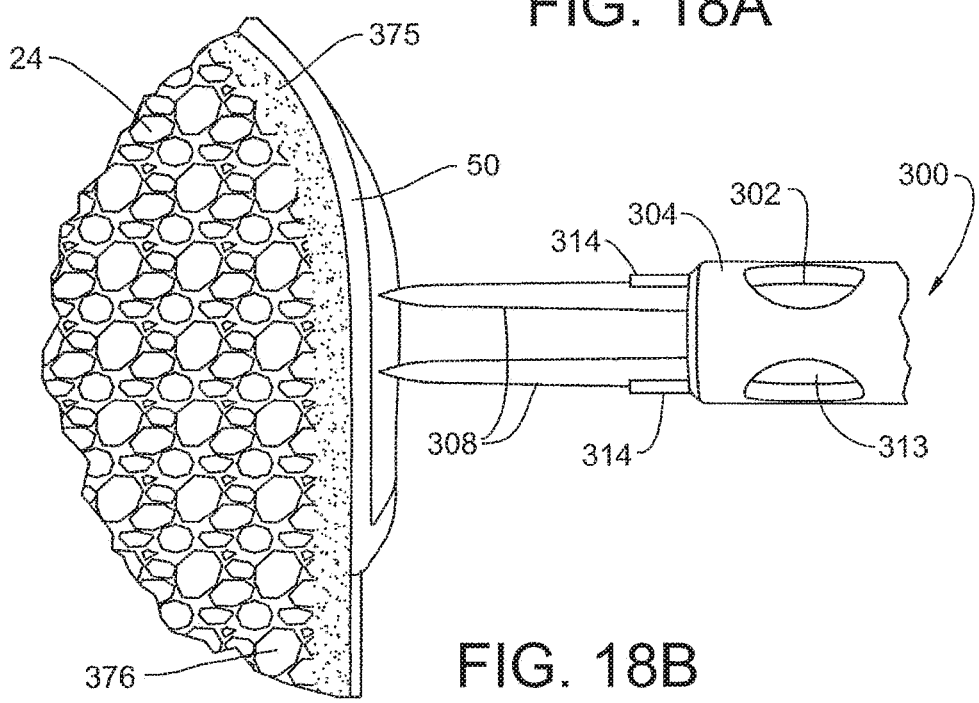
FIG. 18B is a simplified plan view of the distal portion of the trocar assembly as position to create pilot holes for affixing the implant to bone in a further step of a method of the disclosure.

FIG. 18B is a schematic illustration of a cross-sectional side view of the partially affixed implant of FIG. 18A showing the small portion of the implant 50 that is not yet affixed to the humeral head 24. As can be seen in the illustration, the humeral head 24 is shown in cross-section which illustrates the composite nature of bone structure. In general, bone includes hard outer portion or cortical layer 375 and a porous softer inner portion or cancellous bone 376. The pilot hole forming trocar assembly 300 is positioned with the spikes 308 over a selected position on the implant 50. As previously discussed, the trocar 302 is positioned within the lumen of the position retention sleeve 304 with spikes 308 extending distally. The spikes 308 can be used to manipulate and position the implant as needed. Once in position, the spikes 308 can be driven into the bone.

Figure 18C:
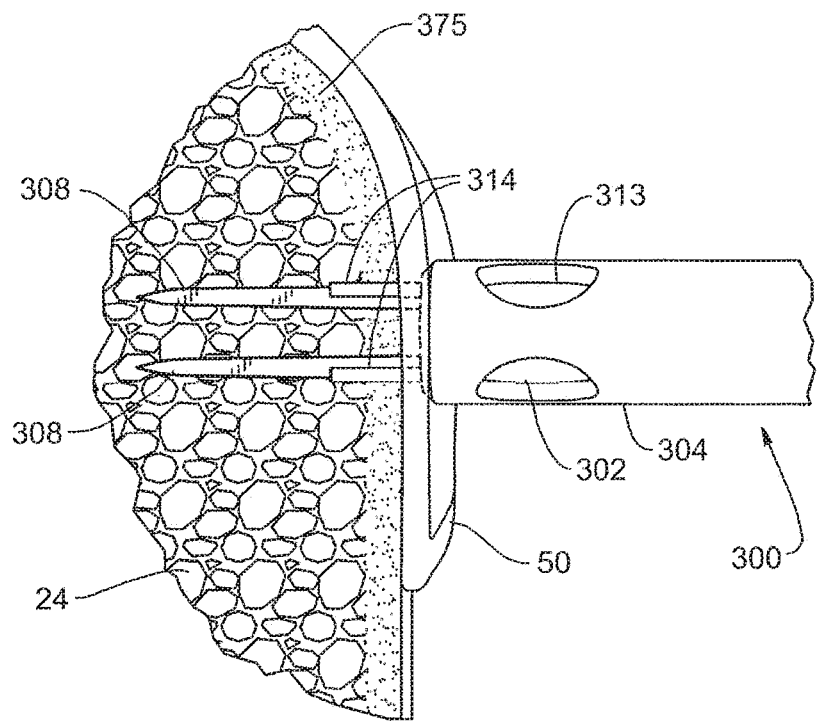
FIG. 18C depicts the trocar assembly of FIG. 18B as inserted into the bone to form pilot holes in accordance with a method of the disclosure.
Figure 18D:
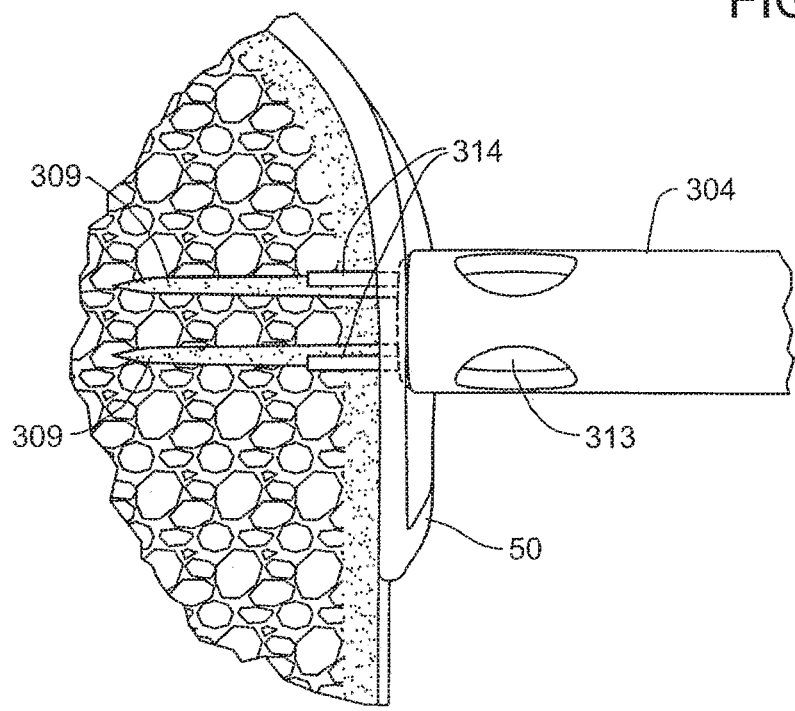
FIG. 18D depicts the trocar assembly with the trocar portion removed and the remaining sheath assembly retaining its position in the pilot holes formed.
Figure 18E:
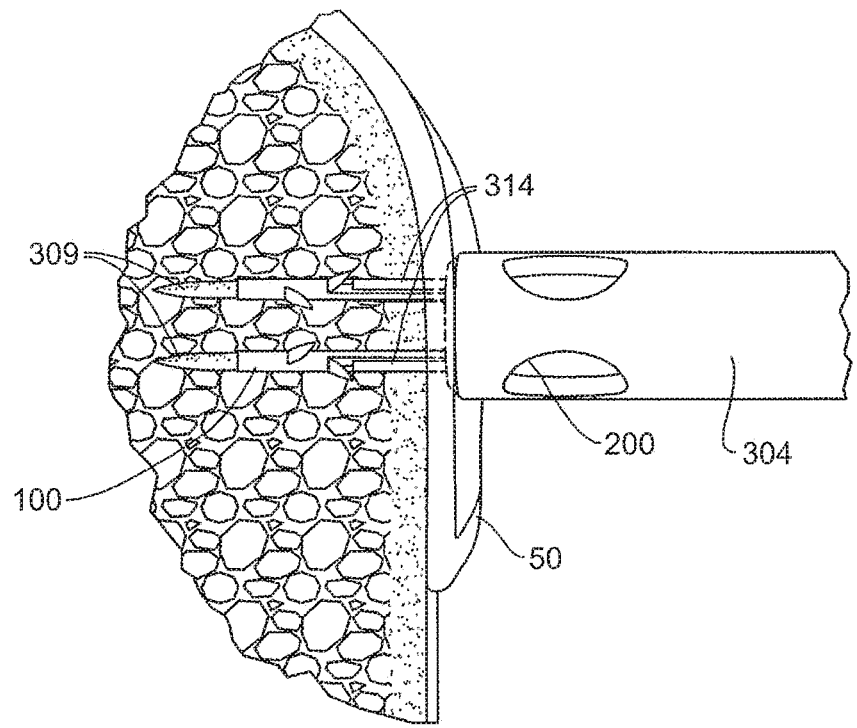
FIG. 18E is a partial perspective view of the articular side of the supraspinatus tendon illustrating the position relative to the biceps tendon and a marker inserted from the bursal side to identify the location of the biceps tendon which is not visible from the bursal side.
Figure 18F:
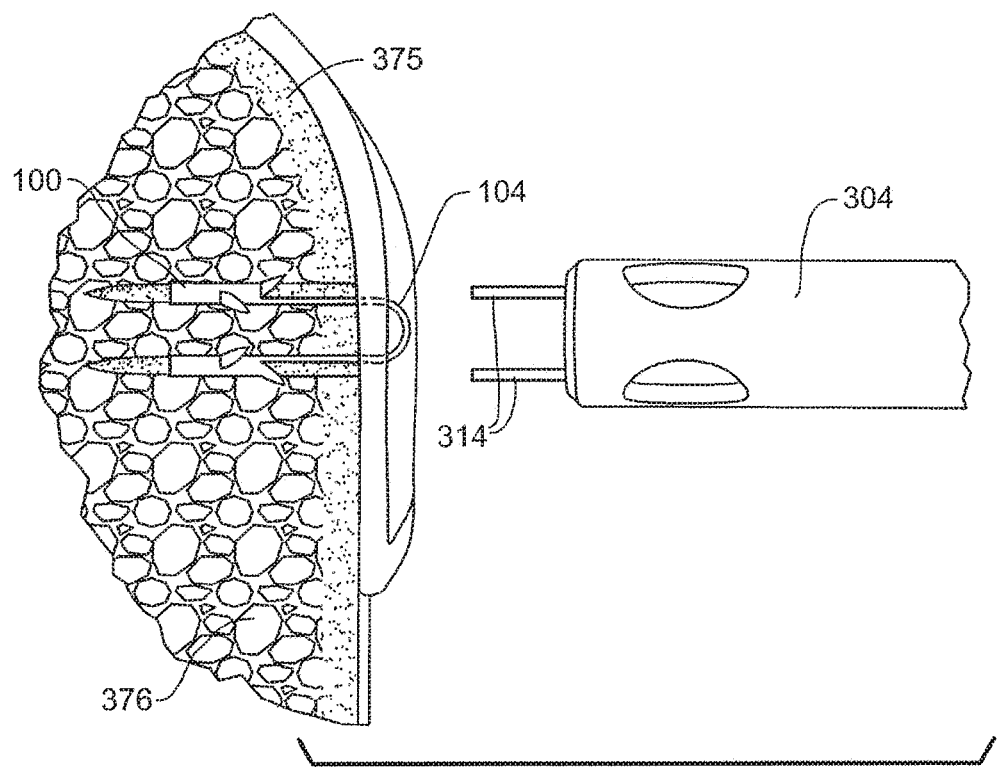
FIG. 18F illustrates a fastener or staple as inserted in accordance with a method of the disclosure.

Referring to FIG. 18C, the illustration of FIG. 18B is re-illustrated with the pilot hole forming trocar 300 spikes pounded or otherwise driven into the humeral head 24, penetrating the cortical layer 375 into the cancellous portion 376. As illustrated, position retention members 314 also penetrate the bone with the spikes 308. In FIG. 18D, it is illustrated that the trocar 302 and its distal spikes 308 are now removed leaving formed pilot holes 309 with the position retention sleeve 304 remaining in position with position retention member 314 extending into pilot holes 309. The position retention member 304 lumen provides a guide to the pilot holes 309 for a staple delivery device 200. In FIG. 18E, a staple 100 is shown extending into the pilot holes 309 as mounted on the distal end of a staple delivery device 200 that has been inserted into the lumen of position retention member 304. In this position the staple can be delivered and retained in the tissue or bone as previously described in the various embodiments disclosed herein. FIG. 18F depicts a staple 100 as delivered into bone with bridge 304 holding the implant in position on the bone and arms of the staple retaining position in the in the bone, such as within the cancellous portion 376.

While exemplary embodiments of the present invention have been shown and described, modifications may be made, and it is therefore intended in the appended claims and subsequently filed claims to cover all such changes and modifications which fall within the true spirit and scope of the invention.

What is claimed is:

1. A method of securing an implant to tissue or bone, comprising:
    positioning the implant at a treatment site;
    driving a pilot hole forming assembly through the implant and into the tissue or bone to form first and second pilot holes in the tissue or bone; and
    inserting a first arm of a fastener through the implant into the first pilot hole and a second arm of the fastener through the implant into the second pilot hole;
    wherein the fastener further includes a bridge connecting a proximal end of the first arm and a proximal end of the second arm, wherein each of the first and second arms includes a trunk portion having only one first projection extending from the trunk portion at a first longitudinal location along the trunk portion and the trunk portion having only one second projection extending from the trunk portion at a second longitudinal location along the trunk portion, the second location being spaced apart longitudinally from the first location distal of the first location, the first projection extending away from the trunk portion in a first direction such that a first moment is applied to the trunk portion in response to a pullout force on the bridge, the second projection extending away from the trunk portion in a second direction opposite the first direction such that a second moment is applied to the trunk portion in an opposite direction to the first direction in response to a pullout force on the bridge;
    wherein the trunk portion of each of the first and second arms includes a localized area of weakness at only the second location;
    wherein a first portion of the trunk portion proximal of the area of weakness rotates relative to a second portion of the trunk portion distal of the area of weakness in response to the second moment.

2. The method of claim 1, further comprising:
    after forming the first and second pilot holes, maintaining a portion of the pilot hole forming assembly in the first and second pilot holes;
    wherein the first and second arms of the fastener are inserted along the portion of the pilot hole forming assembly.

3. The method of claim 1, wherein the bridge has a lateral extent less than a lateral extent of each trunk portion.

4. The method of claim 1, wherein each of the first and second arms comprises a non-trunk portion having a reduced lateral stiffness compared to the trunk portion.

5. The method of claim 4, wherein the non-trunk portion has a lateral extent less than a lateral extent of the trunk portion.

6. The method of claim 4, wherein a distal end of the non-trunk portion abuts a proximal end of the trunk portion.

7. The method of claim 6, wherein the change in lateral stiffness at the location where the distal end of the non-trunk portion abuts the proximal end of the trunk portion permits flexing of each trunk portion in response to the first moment.

8. The method of claim 1, wherein the localized area of weakness is formed by a slit formed proximal of the second projection.

9. The method of claim 1, further comprising:
    urging the first and second projections of each of the first and second arms into orientations which lock the fastener into the tissue or bone using the fastener delivery tool.

10. The method of claim 9, wherein urging the first and second projections of each of the first and second arms includes rotating the first and second projections within their respective pilot holes.

11. A method of securing an implant to tissue or bone, comprising:
    positioning the implant at a treatment site;
    driving a pilot hole forming assembly through the implant and into the tissue or bone to form first and second pilot holes in the tissue or bone;
    inserting a first arm of a fastener through the implant into the first pilot hole and a second arm of the fastener through the implant into the second pilot hole;
    wherein the fastener further includes a bridge connecting the first arm and the second arm, wherein each of the first and second arms includes a trunk portion having only one first projection extending from the trunk portion at a first longitudinal location along the trunk portion and the trunk portion having only one second projection extending from the trunk portion at a second longitudinal location along the trunk portion, the second location being spaced apart longitudinally from the first location distal of the first location, the non-trunk portion having a reduced lateral extent compared to the non-trunk portion, the first projection extending away from the trunk portion in a first direction such that a first moment is applied to the trunk portion in response to a pullout force on the bridge, the second projection extending away from the trunk portion in a second direction different from the first direction such that a second moment is applied to the trunk portion in response to the pullout force on the bridge;
    causing rotation of the trunk portion relative to the non-trunk portion by the first moment; and causing rotation of the trunk portion about an area of weakness proximate only the second projection by the second moment.

12. The method of claim 11, wherein different portions of the trunk portion rotate in opposite directions in response to the pullout force on the bridge.

13. The method of claim 11, wherein the first direction extends proximally and laterally away from each trunk portion, the second direction extends proximally and laterally away from the each trunk portion and a lateral component of the second direction is generally opposite a lateral component of the first direction.

14. The method of claim 11, wherein the area of weakness is formed by a slit formed proximal of the second projection.

15. A method of securing an implant to tissue or bone, comprising:
- positioning the implant at a treatment site;
- driving a pilot hole forming assembly through the implant and into the tissue or bone to form first and second pilot holes in the tissue or bone;
- inserting a first arm of a staple through the implant into the first pilot hole and a second arm of the staple through the implant into the second pilot hole;
- wherein the staple further includes a bridge connecting the first arm and the second arm, wherein each of the first and second arms includes a trunk portion having:
  - only one first projection extending from the trunk portion at a proximal end of the trunk portion;
  - a single slot extending into the trunk portion intermediate the proximal end of the trunk portion and a distal end of the trunk portion; and
  - only one second projection extending from the trunk portion at the slot;
  - wherein the first projection extends away from the trunk portion in a first direction such that a first moment is applied to the trunk portion in response to a pullout force on the bridge, and
  - wherein the second projection extends away from the trunk portion in a second direction different from the first direction such that a second moment is applied to the trunk portion in response to the pullout force on the bridge; and
- causing a first portion of the trunk portion proximal of the slot to rotate relative to a second portion of the trunk portion distal of the slot in response to the pullout force.

* * * * *